US009024058B2

(12) United States Patent
Nagamori et al.

(10) Patent No.: US 9,024,058 B2
(45) Date of Patent: May 5, 2015

(54) AMMONIUM FLUOROALKANESULFONATES AND A SYNTHESIS METHOD THEREFOR

(75) Inventors: Magashi Nagamori, Fujimino (JP); Yuji Hagiwara, Kawagoe (JP); Takashi Masubuchi, Fujimino (JP); Satoru Narizuka, Saitama (JP)

(73) Assignee: Central Glass Company, Limited, Ube-shi (JP)

( * ) Notice: Subject to any disclaimer, the term of this patent is extended or adjusted under 35 U.S.C. 154(b) by 784 days.

(21) Appl. No.: 13/256,101

(22) PCT Filed: Mar. 12, 2010

(86) PCT No.: PCT/JP2010/054246
§ 371 (c)(1),
(2), (4) Date: Sep. 12, 2011

(87) PCT Pub. No.: WO2010/104178
PCT Pub. Date: Sep. 16, 2010

(65) Prior Publication Data
US 2012/0004447 A1    Jan. 5, 2012

(30) Foreign Application Priority Data

Mar. 13, 2009 (JP) ................................. 2009-061240
Mar. 11, 2010 (JP) ................................. 2010-054089

(51) Int. Cl.
*C07C 309/00* (2006.01)
*C07C 313/04* (2006.01)
(Continued)

(52) U.S. Cl.
CPC ............. *C07C 313/04* (2013.01); *C07C 303/32* (2013.01); *C07C 381/12* (2013.01); *G03F 7/0045* (2013.01); *G03F 7/0046* (2013.01); *G03F 7/0392* (2013.01)

(58) Field of Classification Search
CPC ........................... C07C 307/02; C07C 309/00
USPC ........................................................... 562/39
See application file for complete search history.

(56) References Cited

U.S. PATENT DOCUMENTS 7,611,822 B2    11/2009  Takemoto
7,928,262 B2     4/2011  Kobayashi et al.
(Continued)

FOREIGN PATENT DOCUMENTS

EP    1783148 A1 *  5/2007
EP    1897869 A1 *  3/2008
(Continued)

OTHER PUBLICATIONS

Korean Office Action dated Dec. 20, 2012 (four (4) pages).
(Continued)

*Primary Examiner* — Porfirio Nazario Gonzalez
*Assistant Examiner* — Kofi Adzamli
(74) *Attorney, Agent, or Firm* — Crowell & Moring LLP

(57) ABSTRACT

An ammonium hydroxyfluoroalkanesulfinate is obtained by using an organic base while sulfinating a bromofluoroalcohol with a sulfinating agent. An ammonium hydroxyfluoroalkanesulfonate is obtained by oxidizing the ammonium hydroxyfluoroalkanesulfinate. An onium fluoroalkanesulfonate is obtained by converting the ammonium hydroxyfluoroalkanesulfonate into an onium salt through esterification. This onium fluoroalkanesulfonate is useful as a photoacid generator in chemically amplified resists and the like.

10 Claims, No Drawings

(51) Int. Cl.
*C07C 303/32* (2006.01)
*C07C 381/12* (2006.01)
*G03F 7/004* (2006.01)
*G03F 7/039* (2006.01)

(56) References Cited

U.S. PATENT DOCUMENTS

| | | |
|---|---|---|
| 2003/0194639 A1 | 10/2003 | Miya et al. |
| 2008/0124656 A1 | 5/2008 | Kobayashi et al. |
| 2008/0318160 A1 | 12/2008 | Ohsawa et al. |
| 2009/0069521 A1 | 3/2009 | Nagai et al. |
| 2010/0035185 A1 | 2/2010 | Hagiwara et al. |
| 2010/0255419 A1 | 10/2010 | Kodama et al. |

FOREIGN PATENT DOCUMENTS

| | | | |
|---|---|---|---|
| JP | 2002-214774 | A | 7/2002 |
| JP | 2004-4561 | A | 1/2004 |
| JP | 2004-117959 | A | 4/2004 |
| JP | 2007-145797 | A | 6/2007 |
| JP | 2008-7409 | A | 1/2008 |
| JP | 2008-7410 | A | 1/2008 |
| JP | 2009-7327 | A | 1/2009 |
| JP | 2009-46479 | A | 3/2009 |
| WO | WO 2006/121096 | A1 | 11/2006 |
| WO | WO 2008/029673 | A1 | 3/2008 |
| WO | WO 2008/056795 | A1 | 5/2008 |
| WO | WO 2008/099869 | A1 | 8/2008 |

OTHER PUBLICATIONS

Japanese Office Action dated Feb. 13, 2014 (Two (2) pages).
International Search Report including English language translation dated May 11, 2010 (Three (3) pages).
PCT/ISA/237 Form (Four (4) pages).

* cited by examiner

AMMONIUM FLUOROALKANESULFONATES AND A SYNTHESIS METHOD THEREFOR

TECHNICAL FIELD

The present invention relates to fluorine-containing sulfonates useful as an intermediate for producing a photoacid generator useful as a chemically amplified resist material suitable for a micro-processing technique, particularly for photolithography in steps of producing a semiconductor device and the like, and to a synthesis method therefor. Furthermore, the present invention relates to a method for synthesizing a fluorine-containing onium sulfonates which can function as the photoacid generator.

BACKGROUND OF THE INVENTION

In recent years, the trend toward micro-scale pattern rule has been increasing with the trend toward large-scale integration and high-speed of LSI. The trend toward a shorter wavelength of the exposure light source lies behind it. For example, it has become possible to mass-produce DRAM (dynamic random-access memory) of 64M-bit (processing dimension is 0.25 μm or less) by the wavelength shortening from mercury lamp i-line (365 nm) to KrF excimer laser (248 nm). Furthermore, in order to realize the production of DRAM having integration degrees of 1 G or greater, a lithography using ArF excimer laser (193 nm) has been adopted.

As a resist suitable for such exposure wavelength, "a chemically amplified resist material" has attracted much attention. This contains a radiosensitive acid generator (hereinafter referred to as "photoacid generator") which generates acid by radiation irradiation (hereinafter referred to as "exposure"), and serves as a pattern-forming material that forms a pattern by making a difference in solubility in a developing solution between the exposed portion and the unexposed portion through a reaction using the acid generated by exposure as a catalyst.

Also concerning a photoacid generator used for such a chemically amplified resist material, studies have variously been carried out. It has been found that an acid strength to cleave an acid labile group of resin is not sufficient in the case where a photoacid generator for generating alkane or arenesulfonic acid, as had been employed for a conventional chemically amplified resist material adopting KrF excimer laser as the light source, is used as a component of the above-mentioned ArF-type chemically amplified resist material; in which resolution cannot be done at all or the sensitivity is so poor as to be adapted to the device production.

Therefore, as the photoacid generator for the ArF-type chemically amplified resist material, those that generate perfluoroalkanesulfonic acid high in acid strength are commonly used; however, perfluorooctane sulfonic acid and derivatives thereof, which are known as PFOS abbreviated by their initials, bring about problems of stability (non-degradability) stemmed from a C—F bond, and biological concentration and accumulation stemmed from hydrophobicity or lipophilicity. Additionally, perfluoroalkanesulfonic acid having 5 or more carbon atoms and derivatives thereof also cause the above problems.

In order to address such problems regarding PFOS, partially-fluorinated alkanesulfonic acids of which degree of fluorine substitution is reduced have been under development at all locations. For instance, onium alkoxycarbonylfluoromethanesulfonates such as triphenylsulfonium methoxycarbonyldifluoromethanesulfonate (Patent Publication 1), (4-methylphenyl)diphenylsulfonyl t-butoxycarbonyldifluoromethanesulfonate (Patent Publication 2) or triphenylsulfonium (adamant-1-ylmethyl)oxycarbonyldifluoromethanesulfonate (Patent Publication 3) has been developed as an acid generator.

On the other hand, triphenylsulfonium 1,1,3,3,3-pentafluoro-2-benzoyloxypropane-1-sulfonate, which is a kind of an onium alkylcarbonyloxyalkanesulfonate and has an ester bond opposite to that of the above-mentioned onium alkoxycarbonyldifluoromethanesulfonate, and the like have been developed (Patent Publication 4).

The present applicant has found an onium 2-alkylcarbonyloxy-1,1-difluoroethanesulfonate having three less fluorine atoms than the acid generator of the Patent Publication 4 so as to be considered to less affect the environment, and has found that this substance functions as an acid generator exhibiting a high acid strength with the minimum possible number of fluorine atoms and has an excellent compatibility with solvents or resins so as to be useful as the acid generator for the resist material (Patent Publication 5).

In Patent Publication 5, a reaction path as represented by the following equation [1]

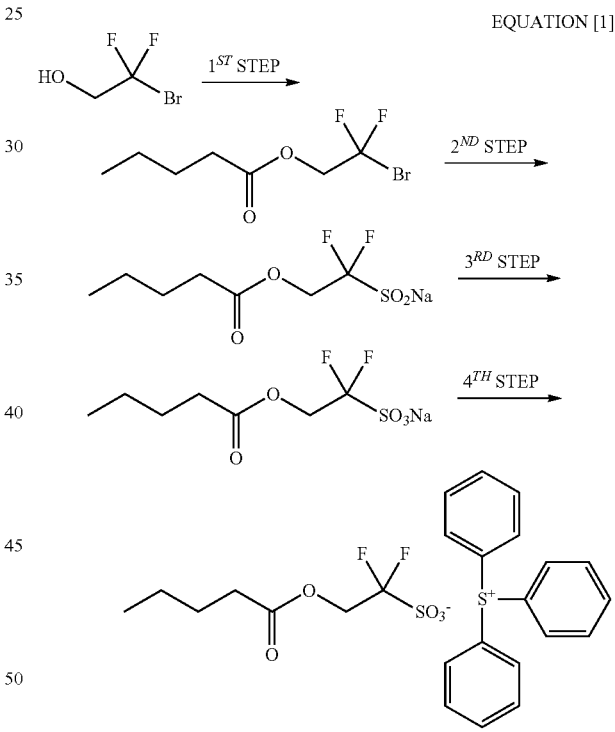

EQUATION [1]

is disclosed as a method for synthesizing an onium 2-alkylcarbonyloxy-1,1-difluoroethanesulfonate. More specifically, the path includes: a first step of reacting bromodifluoroethanol with a carboxylic chloride thereby obtaining a corresponding ester; a second step of sulfinating the obtained ester with a sulfinating agent thereby obtaining a metal sulfinate; a third step of oxidizing the obtained metal sulfinate with an oxidizing agent thereby obtaining a metal sulfonate; and a fourth step of reacting the obtained metal sulfonate with a monovalent onium salt thereby obtaining an onium sulfonate.

Furthermore, the present applicant has found a polymerizable onium tetrafluoroalkanesulfonate, which is a similar onium alkylcarbonyloxyalkanesulfonate but nevertheless one having one less fluorine atom than the acid generator of the Patent Publication 4 so as to be considered to less affect the environment (Patent Publication 6).

In Patent Publication 6, a reaction path as represented by the following equation [2]

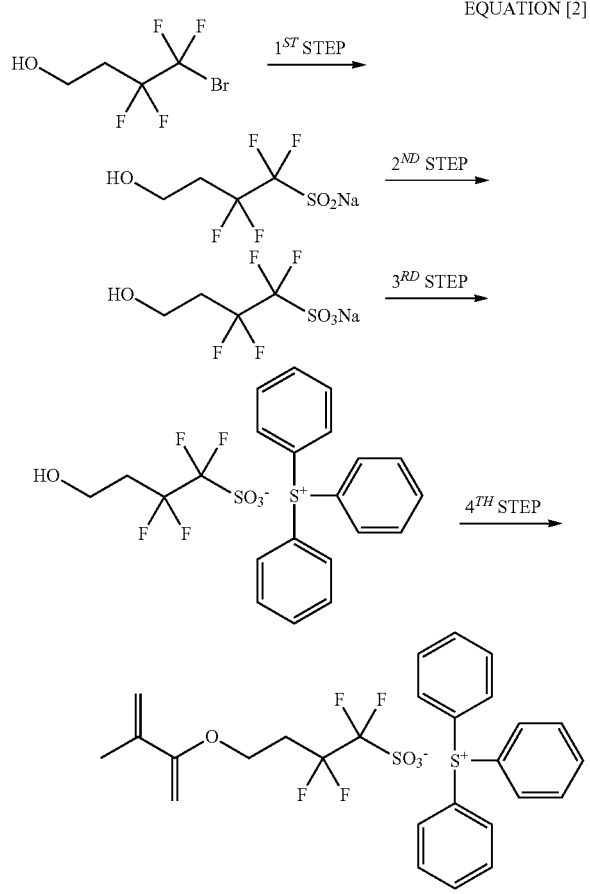

is disclosed as a method for synthesizing the polymerizable onium tetrafluoroalkanesulfonate. More specifically, the path includes: a first step of sulfinating 4-bromo-3,3,4,4-tetrafluorobutan-1-ol with a sulfinating agent thereby obtaining a metal sulfinate; a second step of oxidizing the obtained metal sulfinate with an oxidizing agent thereby obtaining a metal sulfonate; a third step of reacting the obtained metal sulfonate with a monovalent onium salt thereby obtaining an onium sulfonate; and a fourth step of reacting the obtained onium sulfonate with an alkyl acrylic acid halide or alkyl acrylic acid anhydride thereby obtaining a target polymerizable onium sulfonate.

Additionally, a similar onium tetrafluoroalkanesulfonate is disclosed also in other publication (Patent Publication 7). In this publication, 1,4-dibromo-1,1,2,2-tetrafluorobutane is prepared as the starting material and is converted into a 4-bromo-3,3,4,4-tetrafluorobutyl ester of aliphatic or aromatic carboxylic acid by undergoing selective substitution reaction using a carboxylic acid salt such as sodium carboxylate and ammonium carboxylate. The ester is then reacted with a sulfinic acid-forming agent such as sodium dithionite in a solvent such as water, acetonitrile and a mixture of these in the presence of a base such as sodium hydrogencarbonate thereby obtaining a 4-acyloxy-1,1,2,2-tetrafluorobutanesulfinic acid salt, just as Patent Publication 6. Thereafter, it was customarily oxidized with an oxidizing agent such as aqueous hydrogen peroxide in water serving as a solvent in the presence of sodium tungstate or the like.

REFERENCES ABOUT PRIOR ART

Patent Publication

Patent Publication 1: Japanese Patent Application Publication No. 2004-117959
Patent Publication 2: Japanese Patent Application Publication No. 2002-214774
Patent Publication 3: Japanese Patent Application Publication No. 2004-004561
Patent Publication 4: Japanese Patent Application Publication No. 2007-145797
Patent Publication 5: Japanese Patent Application Publication No. 2009-007327
Patent Publication 6: International Application Publication 2008/056795 Pamphlet
Patent Publication 7: Japanese Patent Application Publication No. 2008-007410

SUMMARY OF THE INVENTION

The method for synthesizing an onium fluoroalkanesulfonate having two or more fluorine atoms, as discussed in Patent Publication 5 and represented by the above-mentioned equation [1], has great difficulty in advancing the sulfination reaction of the second step and therefore not only takes a long period of time (several tens of hours) to accomplish the reaction but also requires the addition of base or sulfinating agent because the reaction stops advancing in progress. In the case where a reaction liquid can be separated into two layers (an organic layer and a water layer) such as a combination of acetonitrile and water, the reaction may not be accomplished unless the water layer is separated from the reaction liquid with another addition of water and the sulfinating agent during the reaction. Furthermore, not only the yield of the reaction is extremely low but also the purity is low.

Additionally, the purity of sodium sulfonate obtained in the oxidation step subsequent to the sulfination step is low.

Moreover, Patent Publication 5 does not discuss an example of acyl group having a polymerizable double bond.

Also in the method as discussed in Patent Publication 6 and represented by the above-mentioned equation [1], the purities of target compounds obtained in the first step, i.e., the sulfination step and the second step, i.e., the oxidation step are low (80% and 78%). In addition to this, the yields are calculated at 77% and 88%, respectively, from the weights of the obtained target compounds with no thought on the purities; however, these are calculated at 62% and 69%, respectively, with thought on the purities, which are not necessarily high. Furthermore, most of impurities are sodium salts, which are inadequate to remain in a photoacid generator in an end product.

Additionally, the third step of the method as discussed in Patent Publication 6 and represented by the above-mentioned equation [1] involves an onium salt-using exchange thereby forming a photosensitive compound; therefore, the two steps, i.e., the third and fourth steps must be conducted under a light-tight condition, so that facilities therefor become a considerable burden. However, Patent Publication 6 discloses it is not possible to perform esterification at the early stage of the third step.

The principal reason for causing such problems resides in the fact that target compounds, i.e., metal sulfinate and metal sulfonate are liable to dissolve in water while being hard to dissolve in organic solvents. In both cases of Patent Publication 5 and Patent Publication 6, acetonitrile is used as an extraction solvent in the sulfination step. This is because other water-insoluble organic solvents have difficulty in sufficiently dissolving or extracting the target metal sulfinate. However, the target metal sulfinate is soluble in water and therefore not so high in recovery of substance extracted therefrom, which results in reduction of the yield of the target product. Moreover, water is dissolved in an acetonitrile layer so that contamination of inorganic impurities tends to occur. Furthermore, water is used in the oxidation step as a reaction solvent and additionally the water is distilled off. In this case, nonvolatile substances in particular among generated impurities are concerned since it is impossible to remove metal salts such as sodium salts.

The method of Patent Publication 7 also provides an yield not necessarily high, so there lies a similar problem.

As had been discussed, there are some harms in producing the onium fluoroalkanesulfonate. Accordingly, it had been desired to establish an industrial synthesis method which can produce a skeleton of the onium fluoroalkanesulfonate readily and reasonably.

In view of the above, an object of the present invention is to provide a method for reasonably and readily producing fluoroalkanesulfonates useful as a photoacid generator or the like used for a chemically amplified resist material.

The present inventors had eagerly made studies in order to achieve the above object. As a result, the inventors have found a novel reaction route useful in producing the onium fluoroalkanesulfonate and extremely advantageous to a large-scale synthesis as compared with the conventional methods.

The present invention involves [Embodiment 1] to [Embodiment 3] as will be discussed below.

Embodiment 1

First of all, studies were made on a method for synthesizing an ammonium hydroxyfluoroalkanesulfinate serving as a raw material compound commonly used throughout the whole of the present invention.

In order to sulfinate an end bromodifluoroalkyl group to obtain an end difluoroalkylsulfinate, there has hitherto been adopted a general method using sodium dithionite as a sulfinating agent in a mixture solvent of water and a polar solvent such as N,N-dimethylformamide (DMF), acetonitrile and methanol. In this case, a sulfinated substance is obtained in the form of a sodium sulfinate (see Journal of Fluorine Chemistry, Volume 67, pages 233-234, 1994, for example).

Also in the case of a bromofluoroalcohol serving as the raw material compound used in the present invention, and represented by the following general formula [1], a corresponding sodium sulfinate represented by the following general formula [9] should be obtained by using sodium dithionite in the mixture solvent of water and the polar solvent such as DMF, acetonitrile and methanol.

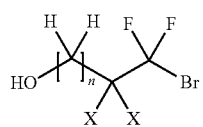

[1]

(In the general formula [1], X mutually independently represents a hydrogen atom or fluorine atom. n represents an integer of 0 to 8.)

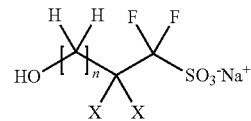

[9]

(In the general formula [9], X mutually independently represents a hydrogen atom or fluorine atom. n represents an integer of 0 to 8.)

However, in the case where n equals 2 and both of the two X are fluorine atoms (i.e., the case of Patent Publication 6), the yield and purity of the sodium sulfinate both are not necessarily high. Additionally, the reaction time extends over 10 hours or greater, which is so long.

Furthermore, in the case where n equals 0 and both of the two X are hydrogen atoms, a target sodium sulfinate is extremely poor in yield and purity both (see Comparative Example 1).

Additionally, bromine that has gotten out of a raw material carboxylic acid bromofluoroalkyl ester is present in this reaction system upon being converted into sodium bromide possibly by sodium of sodium dithionite, which had brought about a lot of problems; for example, if condensation is conducted without removing this bromine or if the bromine is brought into the next step (i.e., an oxidation step) without being separated from a target sodium sulfinate, a by-product is sometimes generated.

In view of the above, the present inventors have eagerly made studies thereon. As a result, they had found that a sodium salt is not obtained but generally only an ammonium salt is obtained by adding amine of not smaller than the equivalent amount of the bromofluoroalcohol together with a sulfinating agent at the time of a sulfination reaction. The ammonium salt is represented by the following general formula [2].

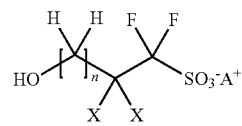

[2]

(In the general formula [2], $A^+$ represents an ammonium ion. X mutually independently represents a hydrogen atom or fluorine atom. n represents an integer of 0 to 8.) This ammonium sulfinate is high in lipophilicity and low in hydrophilicity, which has brought the inventors a finding that water-soluble impurities containing inorganic salts can be removed and purified into a high-purity ammonium sulfinate by such a method as to dissolve an unpurified product obtained after the reaction and containing the inorganic salts in a suitable organic solvent and to separate an undissolved content by filtration. They have further found it is possible to excellently suppress the generation of a by-product (a carboxylic acid bromofluoroalkyl ester serving as a substrate for the sulfination reaction and represented by the general formula [1]; it is gone during a sulfination step but regenerated during the oxidation step) which is to be generated in a subsequent "oxidation step" (see Comparative Example 3).

Furthermore, the present inventors have achieved an amazing fact that the sulfination reaction is excellently accelerated by the coexistence of the amine so as to be finished in a short time.

The present inventors have thus found a synthesis method suitable for a large-scale production of a hydroxyfluoroalkanesulfinate useful as an intermediate for producing a photoacid generator for use in a resist or as an intermediate for producing a solid polymer electrolyte for use in a fuel cell, and a purification method therefor.

Embodiment 2

The ammonium hydroxyfluoroalkanesulfinate obtained by the method as discussed in [Embodiment 1] (the method is also referred to as "a first step") and represented by the general formula [2] is put through the oxidation step (a second step). It has been found that an ammonium hydroxyfluoroalkanesulfonate represented by the following general formula [3] is obtained thereby.

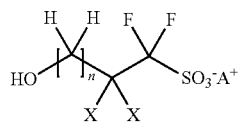
[3]

(In the general formula [3], $A^+$ represents an ammonium ion. X mutually independently represents a hydrogen atom or fluorine atom. n represents an integer of 0 to 8.)

This ammonium sulfonate is high in lipophilicity and low in hydrophilicity, similar to the above-mentioned ammonium sulfinate. Accordingly, the inventors have reached a finding that water-soluble impurities containing inorganic salts can be removed and purified into a high-purity ammonium sulfonate by such a method as to dissolve an unpurified product obtained after the reaction and containing the inorganic salts in a suitable organic solvent and to separate an undissolved content by filtration.

The present inventors have thus found a synthesis method suitable for a large-scale production of a hydroxyfluoroalkanesulfonate useful as an intermediate for producing a photoacid generator for use in a resist or as an intermediate for producing a solid polymer electrolyte for use in a fuel cell, and a purification method therefor.

Embodiment 3

The ammonium hydroxyfluoroalkanesulfonate obtained by the above-mentioned [Embodiment 2] and represented by the general formula [3] is reacted with a carboxylic acid derivative represented by the general formula [6] or the general formula [7], thereby obtaining an ammonium fluoroalkanesulfonate represented by the general formula [4]. Moreover, an onium salt-exchange is conducted thereon in the use of a monovalent onium salt represented by the general formula [8]. It has been found that an onium fluoroalkanesulfonate useful as a photoacid generator for use in a resist and represented by the general formula [5] is obtained thereby.

[6]

(In the general formula [6], X' represents a hydroxyl group or a halogen. R represents a linear or branched alkyl group having 1 to 10 carbon atoms, a linear or branched alkenyl group having 1 to 10 carbon atoms and a polymerizable double bond at least at the end moiety, an alicyclic organic group having 3 to 20 carbon atoms, an organic group having 3 to 20 carbon atoms and containing an alicyclic organic group and a linear alkylene group, a monocyclic or polycyclic lactone having 3 to 30 carbon atoms, or an aryl group having 6 to 20 carbon atoms. (In this formula, some or all of hydrogen atoms disposed in the alkyl group, the alkenyl group, the alicyclic organic group, the organic group containing the alicyclic organic group and the linear alkylene group, the monocyclic or polycyclic lactone or the aryl group may be substituted with fluorine, a hydroxyl group, a hydroxycarbonyl group, or a linear, branched or cyclic alkoxy group having 1 to 6 carbon atoms. Additionally, two hydrogen atoms disposed on the same carbon that constructs the alkyl group, the alkenyl group, the alicyclic organic group, or the organic group containing the alicyclic organic group and the linear alkylene group may be substituted with one oxygen atom to form a keto group. Furthermore, one of hydrogen atoms disposed on the alkyl group may be substituted with 2-acryloyloxy group or a 2-methacryloyloxy group.))

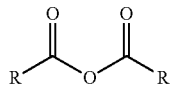
[7]

(In the general formula [7], R is synonymous with R of the general formula [6].)

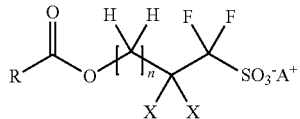
[4]

(In the general formula [4], $A^+$ represents an ammonium ion. X mutually independently represents a hydrogen atom or fluorine atom. n represents an integer of 0 to 8. R is synonymous with R of the general formula [6].)

$Q^+X^-$ [8]

(In the general formula [8], $X^-$ represents a monovalent anion. $Q^+$ represents a sulfonium cation shown in the following general formula (a) or general formula (b), or an iodonium cation shown in the following general formula (c).

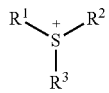
(a)

In the general formula (a), $R^1$, $R^2$ and $R^3$ mutually independently represent a substituted or unsubstituted linear or branched alkyl group, alkenyl group or oxoalkyl group having 1 to 10 carbon atoms, or a substituted or unsubstituted aryl group, aralkyl group or aryloxoalkyl group having 6 to 18 carbon atoms. Alternatively, two or more of $R^1$, $R^2$ and $R^3$ may bond to each other to form a ring together with a sulfur atom shown in the formula.

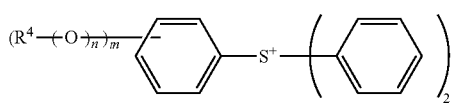
(b)

In the general formula (b), $R^4$ represents a substituted or unsubstituted linear, branched or cyclic alkyl group or alkenyl group having 1 to 20 carbon atoms, or a substituted or unsubstituted aryl group having 6 to 14 carbon atoms. m represents an integer of 1 to 5, and n represents 0 (zero) or 1.

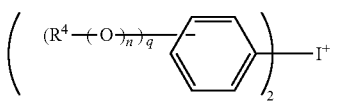
(c)

In the general formula (c), $R^4$ represents a substituted or unsubstituted linear, branched or cyclic alkyl group or alkenyl group having 1 to 20 carbon atoms, or a substituted or unsubstituted aryl group having 6 to 14 carbon atoms. q represents an integer of 0 (zero) to 5, and n represents 0 (zero) or 1.)

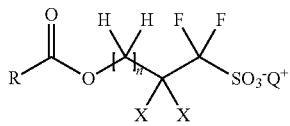
[5]

In other words, it has become possible to synthesize the onium fluoroalkanesulfonate useful as a photoacid generator used for a chemically amplified resist material, by the method as discussed in [Embodiment 3].

In the onium fluoroalkanesulfonate represented by the general formula [5], an important point is that the substituent R involves "those that have an unconjugated unsaturated moiety (a double or triple bond) in its structure". Such a substituent R may be exemplified by polymerizable double bond-containing groups as represented by the following formulas.

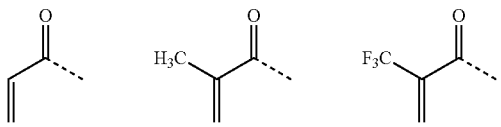

The method of Patent Publication 5 (Japanese Patent Application Publication No. 2009-007327) cannot be applied to a compound having an unconjugated unsaturated moiety at an acyloxy moiety of the onium fluoroalkanesulfonate, though it is useful (Comparative Example 2).

In other words, the [Embodiment 3] is particularly useful for those having in its structure the unconjugated unsaturated moiety as the substituent R, among onium fluoroalkanesulfonates useful as a photoacid generator used for a chemically amplified resist material.

In particular, those that have the unconjugated unsaturated moiety at the end of the substituent, i.e., an onium (w-alkenylcarbonyloxy)fluoroalkanesulfonate, can be fixed in a resist resin by being copolymerized with other monomer and therefore can be used as "a photoacid generator of a type carried on the resist resin", as disclosed in a pamphlet of International Patent Application Publication No. 2006/121096. Such a "photoacid generator of the type carried by the resist resin" is a new type of photoacid generator that has recently been receiving attention because of its high performances such as a high resolution. Also in such a sense, the onium (ω-alkenylcarbonyloxy)fluoroalkanesulfonate having the unconjugated unsaturated moiety at the end of the substituent is extremely useful.

Additionally, another feature of the Embodiment 3 resides in the order of a formerly performed esterification and a latterly performed onium salt-exchange. In the method of the above-mentioned Patent Publication 6 (International Application Publication 2008/056795 Pamphlet), the onium salt-exchange is performed formerly, followed by esterification; hence, steps that must be conducted under a light-tight condition take a long period of time and therefore a burden of facilities is considerable (since the less facilities provided under such a specific condition as the light-tight condition, the more preferable it is. The longer the time of the steps became, the more facilities under the light-tight condition are to be necessitated). However, in the method of Patent Publication 6, it is not possible to perform esterification formerly and the onium salt-exchange latterly.

As discussed above, a suitable adoption of [Embodiment 1] to [Embodiment 3] makes it possible to produce the fluoroalkanesulfonate useful as the intermediate for the acid generator used in the resist material or as the intermediate for the electrolyte for the fuel cell, and more specifically, the onium fluoroalkanesulfonate useful as the photoacid generator, with regard to compounds of wide kinds of substituents, with which the present invention has achieved completion.

The present invention, in which all necessary raw materials are reasonable and operations of any of the steps are so convenience as to be able to perform with a less operational burden, is much more advantageous than the conventional means from the viewpoint of the industrial-scale production of target fluoroalkanesulfonates.

More specifically, the present invention involves [Invention 1] to [Invention 10].

[Invention 1]

A method for synthesizing an ammonium hydroxyfluoroalkanesulfinate represented by the general formula [2], comprising the step of:

reacting a bromofluoroalcohol represented by following the general formula [1] with a sulfinating agent in the presence of amine.

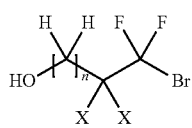
[1]

-continued

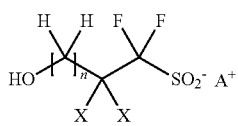  [2]

(In the general formula [1] and the general formula [2]; A⁺ represents an ammonium ion; X mutually independently represents a hydrogen atom or fluorine atom; and n represents an integer of 0 to 8.)

[Invention 2]

A method for synthesizing an ammonium hydroxyfluoroalkanesulfonate represented by the general formula [3], comprising the following two steps of:

a 1$^{st}$ step (a sulfination step) of reacting a bromofluoroalcohol represented by the following general formula [1] with a sulfinating agent in the presence of amine thereby obtaining an ammonium hydroxyfluoroalkanesulfinate represented by the general formula [2]; and a 2$^{nd}$ step (an oxidation step) of reacting the ammonium hydroxyfluoroalkanesulfinate represented by the general formula [2] and obtained by the 1$^{st}$ step (the sulfination step) with an oxidizing agent thereby obtaining the ammonium hydroxyfluoroalkanesulfonate represented by the general formula [3].

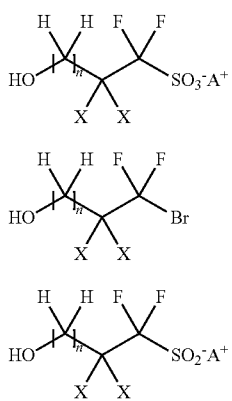

(In the general formula [1] to the general formula [3]: A⁺ represents an ammonium ion; X mutually independently represents a hydrogen atom or fluorine atom; and n represents an integer of 0 to 8.)

[Invention 3]

A method for synthesizing an onium fluoroalkanesulfonate represented by the general formula [5], comprising the steps of:

a 3$^{rd}$ step (an esterification step) of reacting the ammonium hydroxyfluoroalkanesulfonate represented by the general formula [3] and obtained by the method as discussed in Invention 2 with a carboxylic acid derivative represented by the general formula [6] or the general formula [7] thereby obtaining an ammonium fluoroalkanesulfonate represented by the general formula [4]; and a 4$^{th}$ step of performing an onium salt-exchange by using a monovalent onium salt represented by the general formula [8].

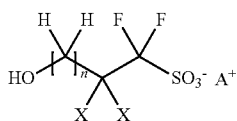  [3]

  [6]

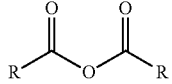  [7]

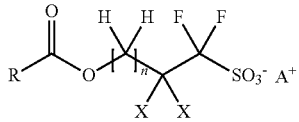  [4]

Q⁺X⁻  [8]

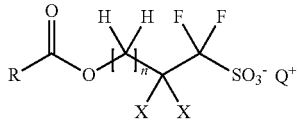  [5]

(In the general formula [3] and the general formula [4], A⁺ represents an ammonium ion. In the general formula [3] to the general formula [5]: X mutually independently represents a hydrogen atom or fluorine atom; and n represents an integer of 0 to 8. In the general formula [6], X' represents a hydroxyl group or a halogen. In the general formula [4] to the general formula [7], R represents a linear or branched alkyl group having 1 to 10 carbon atoms, a linear or branched alkenyl group having 1 to 10 carbon atoms and a polymerizable double bond at least at the end moiety, an alicyclic organic group having 3 to 20 carbon atoms, an organic group having 3 to 20 carbon atoms and containing an alicyclic organic group and a linear alkylene group, a monocyclic or polycyclic lactone having 3 to 30 carbon atoms, or an aryl group having 6 to 20 carbon atoms. (In this formula, some or all of hydrogen atoms disposed in the alkyl group, the alkenyl group, the alicyclic organic group, the organic group containing the alicyclic organic group and the linear alkylene group, the monocyclic or polycyclic lactone or the aryl group may be substituted with fluorine, a hydroxyl group, a hydroxycarbonyl group, or a linear, branched or cyclic alkoxy group having 1 to 6 carbon atoms. Additionally, two hydrogen atoms disposed on the same carbon that constructs the alkyl group, the alkenyl group, the alicyclic organic group, or the organic group containing the alicyclic organic group and the linear alkylene group may be substituted with one oxygen atom to form a keto group. Furthermore, one of hydrogen atoms disposed on the alkyl group may be substituted with 2-acryloyloxy group, a 2-methacryloyloxy group or a 2-trifluoromethacryloyloxy group.) In the general formula [5] and the general formula [8], Q⁺ represents a sulfonium cation shown in the following general formula (a) or the general formula (b), or an iodonium cation shown in the following general formula (c).

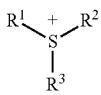

(a)

(In the general formula (a), $R^1$, $R^2$ and $R^3$ mutually independently represent a substituted or unsubstituted linear or branched alkyl group, alkenyl group or oxoalkyl group having 1 to 10 carbon atoms, or a substituted or unsubstituted aryl group, aralkyl group or aryloxoalkyl group having 6 to 18 carbon atoms. Alternatively, two or more of $R^1$, $R^2$ and $R^3$ may bond to each other to form a ring together with a sulfur atom shown in the formula.)

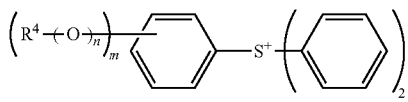

(b)

(In the general formula (b): $R^4$ represents a substituted or unsubstituted linear, branched or cyclic alkyl group or alkenyl group having 1 to 20 carbon atoms, or a substituted or unsubstituted aryl group having 6 to 14 carbon atoms; m represents an integer of 1 to 5; and n represents 0 (zero) or 1.)

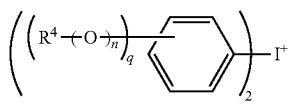

(c)

(In the general formula (c): $R^4$ represents a substituted or unsubstituted linear, branched or cyclic alkyl group or alkenyl group having 1 to 20 carbon atoms, or a substituted or unsubstituted aryl group having 6 to 14 carbon atoms; q represents an integer of 0 (zero) to 5; and n represents 0 (zero) or 1.))

[Invention 4]
A method as discussed in Invention 1, wherein, in the general formula [1] to the general formula [5], n is 2 and both of two X are fluorine atoms.

[Invention 5]
A method as discussed in Invention 1, wherein, in the general formula [1] to the general formula [5], n is 4 and both of two X are fluorine atoms.

[Invention 6]
A method as discussed in Invention 1, wherein, in the general formula [1] to the general formula [5], n is 0 and both of two X are hydrogen atoms.

[Invention 7]
A method as discussed in Invention 1, wherein the amine used in the sulfination step is amine represented by the following general formula [I].

[I]

(In the general formula [I], $G^1$, $G^2$ and $G^3$ mutually independently represent a hydrogen atom, an alkyl group having 1 to 6 carbon atoms, an alkoxyalkyl group having 1 to 6 carbon atoms, a cycloalkyl group having 3 to 12 carbon atoms, a substitution-acceptable phenyl group, a substitution-acceptable aralkyl group having 7 to 12 carbon atoms, a substitution-acceptable naphthyl group, or a substitution-acceptable heteroaromatic group having 5 to 10 carbon atoms. Alternatively, at least two or more of $G^1$, $G^2$ and $G^3$ may form a ring which may include a heteroatom.)

[Invention 8]
A method as discussed in Invention 3, wherein R in the general formula [4] to the general formula [7] represents any one of polymerizable double bond-containing groups represented by the following formulas.

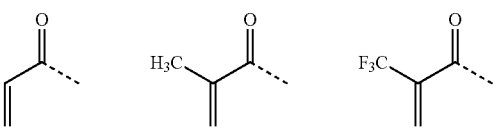

(In the formulas, each dotted line represents a bonding location.)

[Invention 9]
An ammonium hydroxyfluoroalkanesulfinate represented by the following general formula [2].

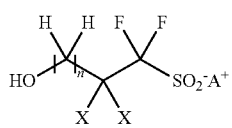

[2]

(In the general formula [2]; $A^+$ represents an ammonium ion; X mutually independently represents a hydrogen atom or fluorine atom; and n represents an integer of 0 to 8.)

[Invention 10]
An ammonium hydroxyfluoroalkanesulfonate represented by the following general formula [3].

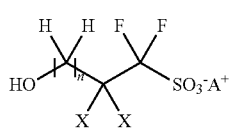

[3]

(In the general formula [3]; $A^+$ represents an ammonium ion; X mutually independently represents a hydrogen atom or fluorine atom; and n represents an integer of 0 to 8.)

DETAILED DESCRIPTION

According to the present invention, there is provided an effect of conveniently producing fluoroalkanesulfonates useful as an intermediate for producing a photoacid generator which intermediate is useful as a chemically amplified resist material suitable for micromachining techniques (e.g. photolithography, in particular) applied in fabrication step of semiconductor devices or the like, or as an intermediate for producing a solid electrolyte used for a fuel cell or the like, at a high yield and on an industrial scale. Furthermore, according to the present invention, there is provided an effect of conveniently producing onium fluoroalkanesulfonates that function as the photoacid generator, at a high yield and on an industrial scale.

Hereinafter, the present invention will be discussed in more detail.

[Ammonium Hydroxyfluoroalkanesulfinate]

An ammonium hydroxyfluoroalkanesulfinate according to the present invention is represented by the following general formula [2].

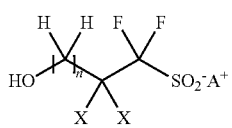

[2]

In the general formula [2], $A^+$ represents an ammonium ion. Concrete examples of the ammonium ion represented by $A^+$ are ammonium ion ($NH_4^+$), methylammonium ion ($MeNH_3^+$), dimethylammonium ion ($Me_2NH_2^+$), trimethylammonium ion ($Me_3NH^+$), ethylammonium ion ($EtNH_3^+$), diethylammonium ion ($Et_2NH_2^+$), triethylammonium ion ($Et_3NH^+$), n-propylammonium ion (n-$PrNH_3^+$), di-n-propylammonium ion (n-$Pr_2NH_2^+$), tri-n-propylammonium ion (n-$Pr_3NH^+$), i-propylammonium ion (i-$PrNH_3^+$), di-i-propylammonium ion (i-$Pr_2NH_2^+$), tri-i-propylammonium ion (i-$Pr_3NH^+$), n-butylammonium ion (n-$BuNH_3^+$), di-n-butylammonium ion (n-$Bu_2NH_2^+$), tri-n-butylammonium ion (n-$Bu_3NH^+$), sec-butylammonium ion (sec-$BuNH_3^+$), di-sec-butylammonium ion (sec-$Bu_2NH_2^+$), tri-sec-butylammonium ion (sec-$Bu_3NH^+$), tert-butylammonium ion (t-$BuNH_3^+$), di-tert-butylammonium ion (t-$Bu_2NH_2^+$), tri-tert-butylammonium ion (t-$Bu_3NH^+$), diisopropylethylammonium (i-$Pr_2EtNH^+$), phenylammonium ion ($PhNH_3^+$), diphenylammonium ion ($Ph_2NH_2^+$), triphenylammonium ion ($Ph_3NH^+$), tetramethylammonium ion ($Me_4N^+$), tetraethylammonium ion ($Et_4N^+$), trimethylethylammonium ion ($Me_3EtN^+$), tetra-n-propylammonium ion (n-$Pr_4N^+$), tetra-i-propylammonium ion (i-$Pr_4N^+$), tetra-n-butylammonium ion (n-$Bu_4N^+$), and ions having the following structures.

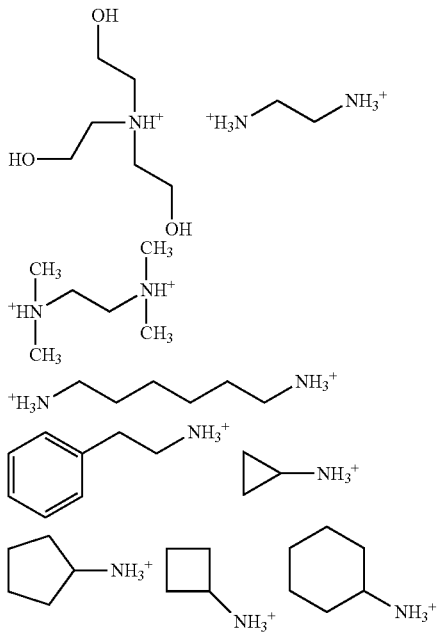

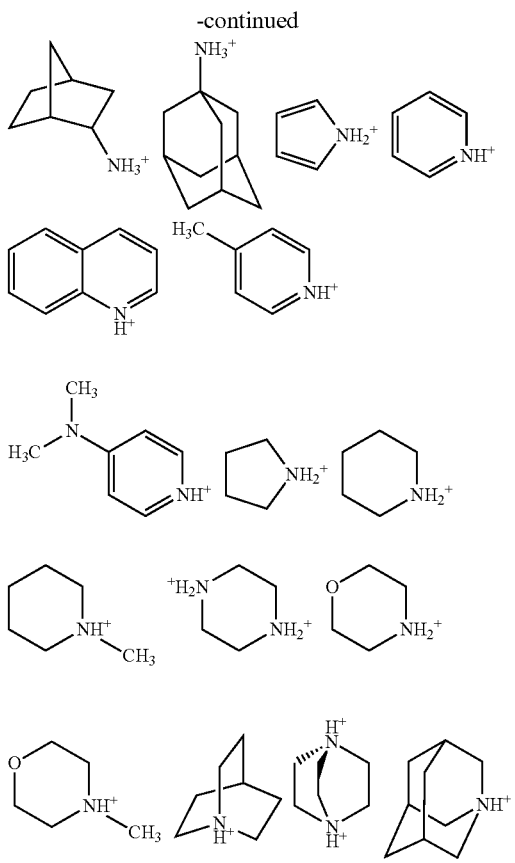

Among these, it is preferable that $A^+$ is an ammonium ion represented by the following general formula [β].

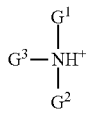

[β]

In the general formula [β], $G^1$, $G^2$ and $G^3$ mutually independently represent a hydrogen atom, an alkyl group having 1 to 6 carbon atoms, an alkoxyalkyl group having 1 to 6 carbon atoms, a cycloalkyl group having 3 to 12 carbon atoms, a substitution-acceptable phenyl group, a substitution-acceptable aralkyl group having 7 to 12 carbon atoms, a substitution-acceptable naphthyl group, or a substitution-acceptable heteroaromatic group having 5 to 10 carbon atoms. Alternatively, at least two or more of $G^1$, $G^2$ and $G^3$ may form a ring which may include a heteroatom.

Concrete examples thereof are trimethylammonium ion ($Me_3NH^+$), triethylammonium ion ($Et_3NH^+$), tri-n-propylammonium ion (n-$Pr_3NH^+$), tri-i-propylammonium ion (i-$Pr_3NH^+$), tri-n-butylammonium ion (n-$Bu_3NH^+$), tri-sec-butylammonium ion (sec-$Bu_3NH^+$), tri-tert-butylammonium ion (t-$Bu_3NH^+$), diisopropylethylammonium (i-$Pr_2EtNH^+$), triphenylammonium ion ($Ph_3NH^+$), and ions having the following structures.

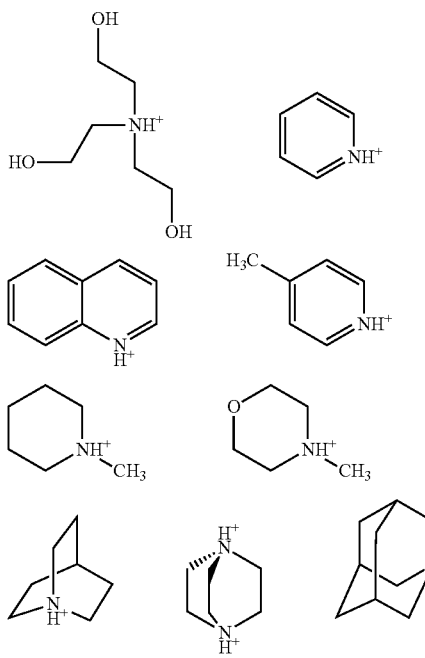

Among these, the particularly preferable are trimethylammonium ion (Me$_3$NH$^+$), triethylammonium ion (Et$_3$NH$^+$) and diisopropylethylammonium (i-Pr$_2$EtNH$^+$).

In the general formula [2], X mutually independently represents a hydrogen atom or fluorine atom. n represents an integer of 0 to 8. The structure of an anion moiety as shown in the general formula [2] is exemplified by the following structures.

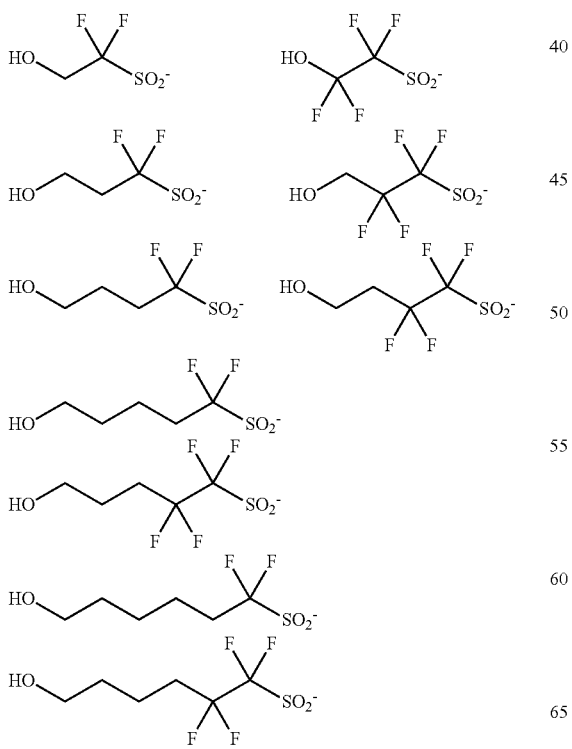

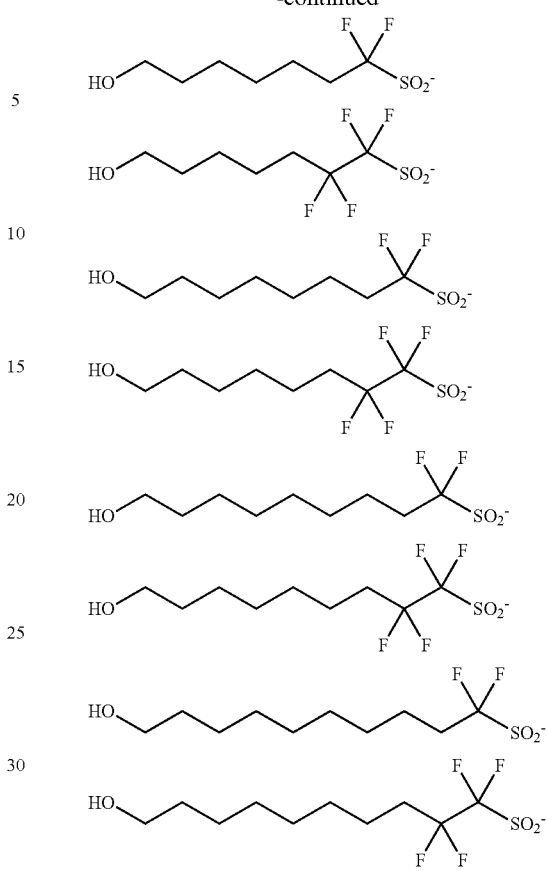

Among combinations of these cations and anions, the particularly preferable ones are exemplified by the following structures.

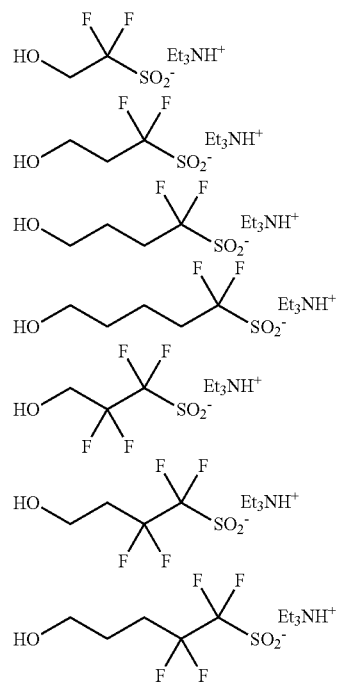

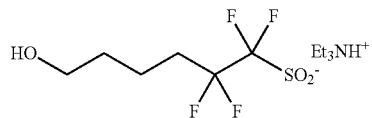

[Ammonium Hydroxyfluoroalkanesulfonate]

An ammonium hydroxyfluoroalkanesulfonate according to the present invention is represented by the following general formula [3].

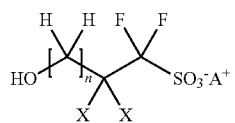

[3]

In the general formula [3], $A^+$ represents an ammonium ion. Incidentally, concrete examples of $A^+$ are those cited in the section of the ammonium hydroxyfluoroalkanesulfinate represented by the general formula [2].

In the general formula [3], X mutually independently represents a hydrogen atom or fluorine atom. n represents an integer of 0 to 8. The structure of an anion moiety as shown in the general formula [3] is exemplified by the following structures.

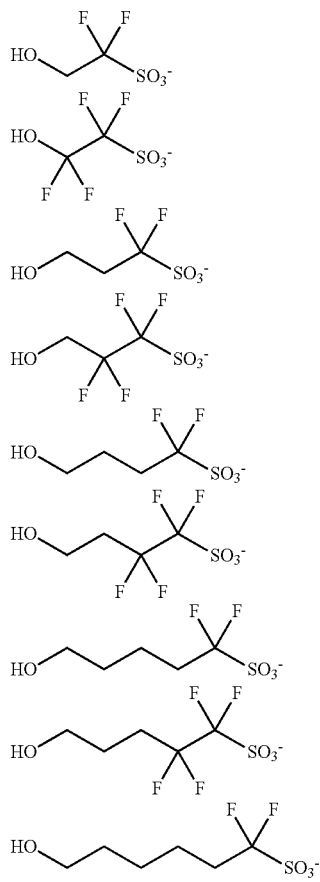

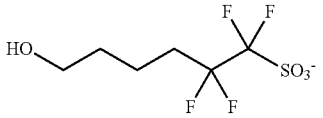

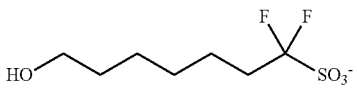

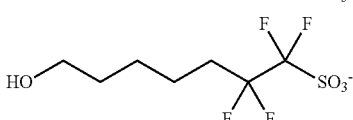

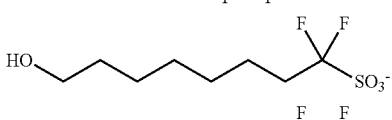

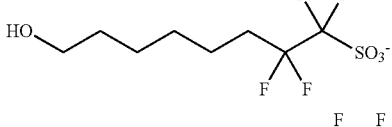

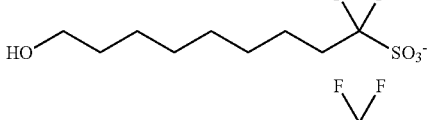

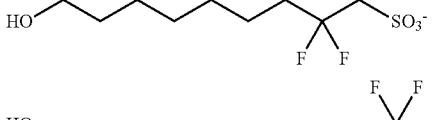

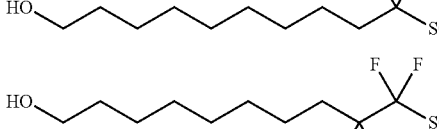

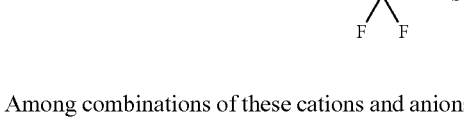

Among combinations of these cations and anions, the particularly preferable ones are exemplified by the following structures.

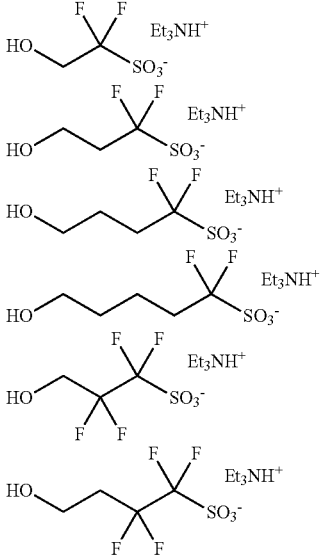

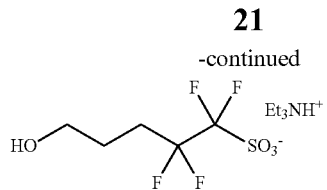

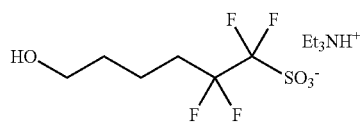

[Outline of Synthesis Method]

Now the invention relating to a synthesis method will be discussed. As shown in the following equation [3], the present invention includes four steps, and more specifically: a step of reacting a bromofluoroalcohol represented by the general formula [1] in the presence of a sulfinating agent and amine thereby obtaining an ammonium hydroxyfluoroalkanesulfinate (a target product of Embodiment 1 of the present invention) represented by the general formula [2] (a 1$^{st}$ step: a sulfination step); a step of reacting the obtained ammonium hydroxyfluoroalkanesulfinate represented by the general formula [2] with an oxidizing agent thereby obtaining an ammonium hydroxyfluoroalkanesulfonate (a target product of Embodiment 2 of the present invention) represented by the general formula [3] (a 2$^{nd}$ step: an oxidation step); a step of esterifying the obtained ammonium hydroxyfluoroalkanesulfonate represented by the general formula [3] through a reaction with a carboxylic acid derivative represented by the general formula [6] or general formula [7] thereby obtaining an ammonium fluoroalkanesulfonate represented by the general formula [4] (a 3$^{rd}$ step: an esterification step); and a step of performing an onium salt-exchange by using a monovalent onium salt represented by the general formula [8], on the obtained ammonium fluoroalkanesulfonate represented by the general formula [4], thereby obtaining an onium fluoroalkanesulfonate (a target product of Embodiment 3 of the present invention) represented by the general formula [5] (a 4$^{th}$ step: an onium salt-exchanging step). Upon undergoing the four steps, an onium fluoroalkanesulfonate having an unconjugated unsaturated moiety (a double or triple bond) as R shown in the general formula [5] can be obtained from a bromofluoroalcohol represented by the general formula [1].

EQUATION [3]

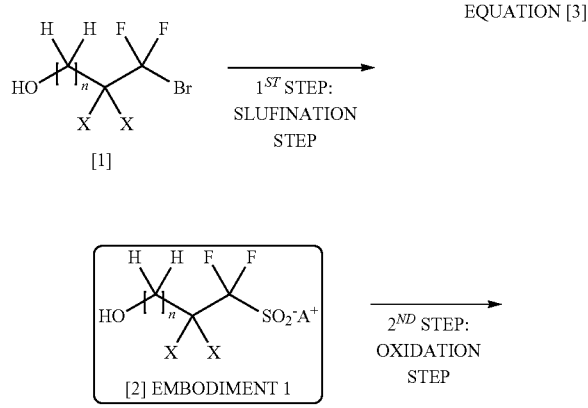

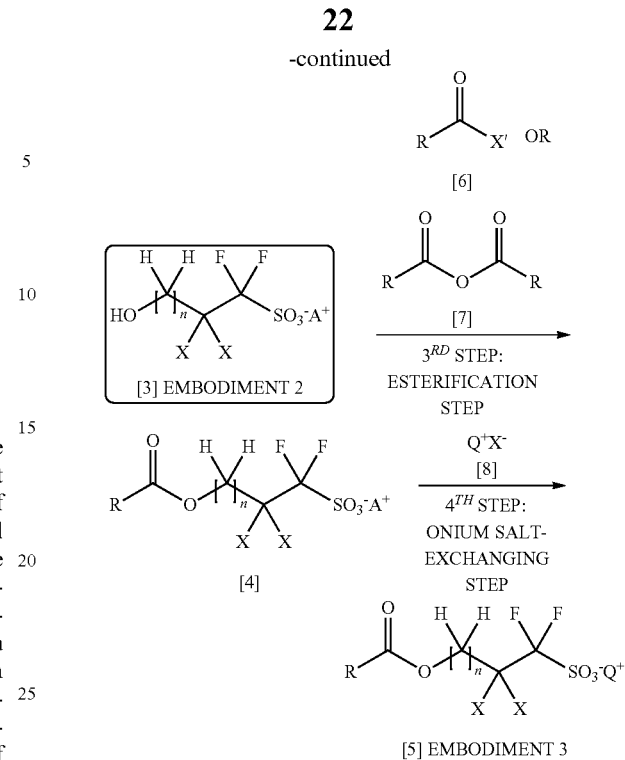

Hereinafter, each of the steps will be discussed in detail.

[1$^{st}$ Step: Sulfination Step]

First of all, a 1$^{st}$ step of the present invention will be discussed. The 1$^{st}$ step is a step of reacting a bromofluoroalcohol represented by the general formula [1] in the presence of a sulfinating agent and an organic base thereby obtaining an ammonium hydroxyfluoroalkanesulfinate (i.e., a sulfination step).

The sulfinating agent used in the present step include those represented by the general formula [10].

$$(S^1)_m(M^1)_n \cdot pH_2O \quad [10]$$

(In the general formula [10], $S^1$ represents $S_2O_4$, $HOCH_2SO_2$, $SO_4$ or $HSO_4$. m and n each represents an integer. p represents 0 (zero) or an integer. $M^1$ represents Li, Na, K or $NH_4$.) Concrete examples thereof are lithium dithionite, sodium dithionite, potassium dithionite, ammonium dithionite, lithium hydroxymethanesulfinate, sodium hydroxymethanesulfinate, potassium hydroxymethanesulfinate, ammonium hydroxymethanesulfinate, lithium sulfite, sodium sulfite, potassium sulfite, ammonium sulfite, lithium hydrogen sulfite, sodium hydrogen sulfite, potassium hydrogen sulfite and ammonium hydrogen sulfite. Among these, sodium dithionite and potassium dithionite are preferable, and sodium dithionite is particularly preferable.

The mole ratio of the sulfinating agent to the bromofluoroalcohol [1] is usually 0.5 to 10, preferably 0.9 to 5.0 and particularly preferably 1.0 to 2.0.

This reaction can be performed also in air, but the sulfinating agent sometimes causes decomposition by water content in the air. It is, therefore, preferable to perform the reaction in a nitrogen or argon atmosphere.

A sulfination reaction using the sulfinating agent may develop without the addition of a base; however, a base is usually added since the reaction can be accelerated thereby. As the base to be added, there are commonly used inorganic bases such as sodium carbonate, potassium carbonate, sodium hydrogencarbonate and potassium hydrogencarbonate. Meanwhile, the present invention uses amines as the base, which is the principal feature of the present invention.

The organic base used (or brought into coexistence) in the present step is a free amine obtained by removing a proton ($H^+$) from each kind of ammonium ions cited above as $A^+$ of the general formula [2]. For example, it is possible to cite ammonia, methylamine, dimethylamine, trimethylamine, ethylamine, diethylamine, triethylamine, n-propylamine, di-n-propylamine, tri-n-propylamine, i-propylamine, di-i-propylamine, tri-i-propylamine, n-butylamine, di-n-butylamine, tri-n-butylamine, sec-butylamine, di-sec-butylamine, tri-sec-butylamine, tert-butylamine, di-tert-butylamine, tri-tert-butylamine, diisopropylethylamine, phenylamine, diphenylamine, triphenylamine, and organic bases having the following structures.

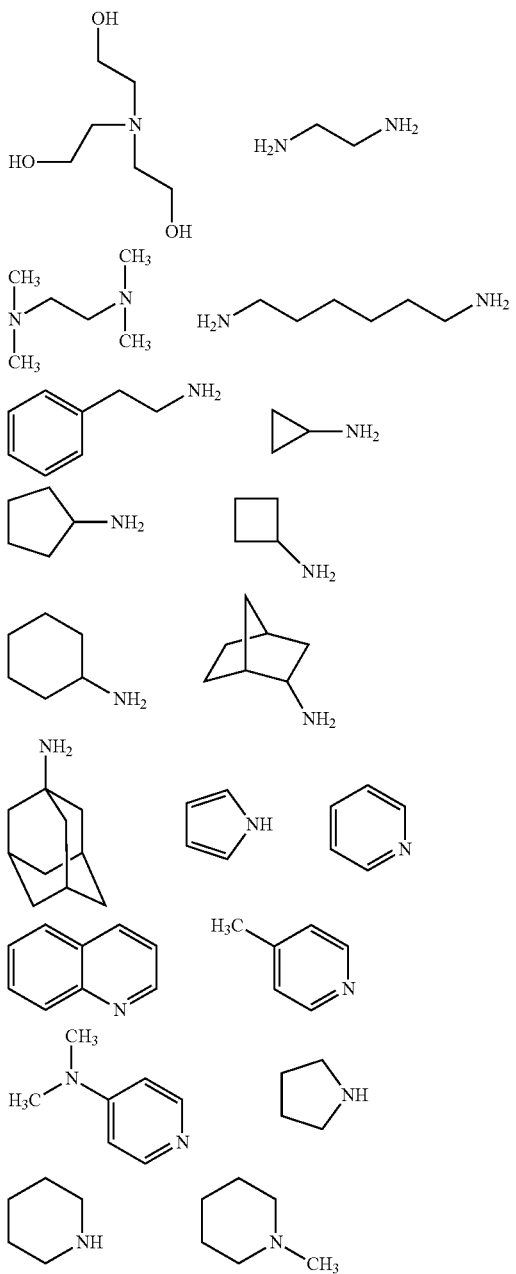

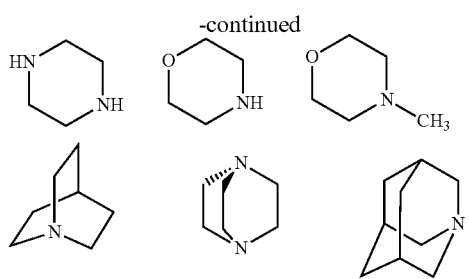

Among these, an amine represented by the general formula [I] is used as a preferable organic base.

[I]

(In the general formula [I], $G^1$, $G^2$ and $G^3$ mutually independently represent a hydrogen atom, an alkyl group having 1 to 6 carbon atoms, an alkoxyalkyl group having 1 to 6 carbon atoms, a cycloalkyl group having 3 to 12 carbon atoms, a substitution-acceptable phenyl group, a substitution-acceptable aralkyl group having 7 to 12 carbon atoms, a substitution-acceptable naphthyl group, or a substitution-acceptable heteroaromatic group having 5 to 10 carbon atoms. Alternatively, at least two or more of $G^1$, $G^2$ and $G^3$ may form a ring which may include a heteroatom.) Concrete examples thereof are trimethylamine, triethylamine, tri-n-propylamine, tri-i-propylamine, tri-n-butylamine, tri-sec-butylamine, tri-tert-butylamine, diisopropylethylamine, triphenylamine, and organic bases having the following structures.

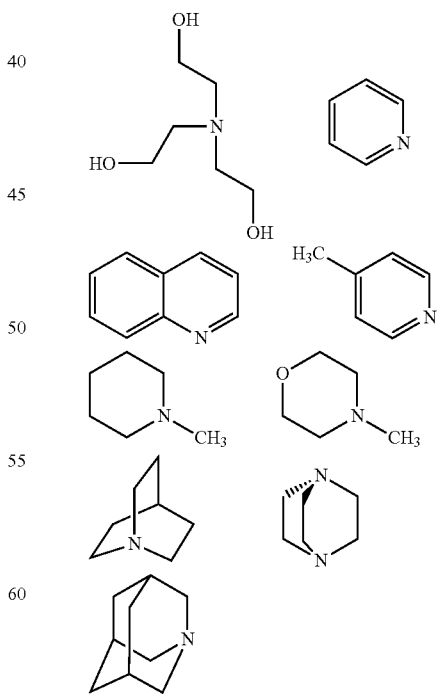

Among these, trimethylamine, triethylamine and diisopropylethylamine are readily available, and furthermore, improve reactivity in the sulfination reaction conspicuously. Additionally, these can sufficiently improve fat-solubility of the ammonium hydroxyfluoroalkanesulfinate obtained thereby, so as to be preferably used.

The mole ratio of the organic base to the bromofluoroalcohol [1] is usually 1.0 to 10.0, preferably 1.1 to 2.0. When the mole ratio is less than 1.0, a metal hydroxyfluoroalkanesulfinate is formed as a by-product by cations derived from the sulfinating agent (e.g. metal cations such as sodium ions, potassium ions and lithium ions). In this case, not only separation of an ammonium salt from the metal salt becomes difficult at a subsequent step but also the yield of the target product is reduced, which is not preferable. A mole ratio exceeding 10.0 is economically disadvantageous so as not to be preferable either, though it can be used without problems.

This reaction is preferably conducted in a mixture solvent of an organic solvent and water. Examples of the organic solvent are those having good compatibility with water, such as lower alcohols, tetrahydrofuran, N,N-dimethylformamide, N,N-dimethylacetamide, acetonitrile and dimethyl sulfoxide. More preferable ones are methanol, N,N-dimethylacetamide, acetonitrile, dimethyl sulfoxide and the like. Particularly preferable one is acetonitrile.

The ratio of the organic solvent to be used to 100 parts by weight of total of the organic solvent and water is usually not less than 5 parts by weight, preferably not less than 10 parts by weight and more preferably 20 to 90 parts by weight.

The reaction temperature is usually 0 to 200° C., preferably 30 to 100° C. The reaction time is usually 0.1 to 12 hours, preferably 0.5 to 6 hours; however, it is further preferable to determine a temporal point at which the raw material bromofluoroalcohol [1] has been consumed as the endpoint of the reaction, by using an analytical device such as thin layer chromatography (TLC) and nuclear magnetic resonance (NMR). In a case where the reaction temperature is higher than the boiling point of the organic solvent or water, a pressure-resistant vessel such as an autoclave is used.

Incidentally, if a comparison concerning the reaction time is made between bromofluoroalcohols [1] having the same structure by using them as substrates, one on which an inorganic base such as sodium carbonate, potassium carbonate, sodium hydrogencarbonate and potassium hydrogencarbonate is used expends a reaction time as much as several times to several tens times that of the other on which the organic solvent is used. More specifically, the former case spends a reaction time of not shorter than 12 hours and sometimes fails to terminate the reaction.

In addition to this, a target sulfinated substance cannot be obtained with a high yield. On the contrary, the case where amine is used as the base can accelerate the reaction significantly and may sometimes terminate the reaction only with several tens of minutes. It is thus possible to shorten the reaction time outstandingly, which is one of the effects achieved by using amines as the base in the present invention.

Then, there will be discussed a treatment conducted after the reaction. In the 1st step of the present invention, fat-solubility of the obtained ammonium hydroxyfluoroalkanesulfinate is improved by using amines as the base. As a result, it becomes possible to dissolve the fat-soluble ammonium hydroxyfluoroalkanesulfinate in the organic solvent by treating an unpurified crude product which contains a great amount of inorganic impurities and obtained upon the reaction, with the organic solvent. At this time, the inorganic impurities contrarily having no fat-solubility can be precipitated and then filtered away. Examples of such a solvent include: halogen-based solvents such as chloroform and dichloromethane; ether-based solvents such as diethyl ether, diisopropyl ether and tert-butyl methyl ether; acetic ester-based solvents such as ethyl acetate and butyl acetate; and ketone-based solvents such as acetone and 2-butanone.

With such a treatment, it becomes possible to increase the purity of a target ammonium hydroxyfluoroalkanesulfinate (see Example 1, Example 2 and Comparative Example 3).

On the other hand, a metal hydroxyfluoroalkanesulfinate obtained by using the inorganic base is inferior in fat-solubility, or rather superior in water-solubility to an ammonium salt. Hence, there is not much difference in fat-solubility between the metal hydroxyfluoroalkanesulfinate and the inorganic impurities desired to be remove, so that it is extremely difficult to selectively singly dissolve the metal hydroxyfluoroalkanesulfinate in the organic solvent as discussed above. The metal hydroxyfluoroalkanesulfinate cannot be obtained at a high purity. Furthermore, if the residual bromine contained in the inorganic substance is not removed, problems are raised in the subsequent step as discussed above. Thus, increase of fat-solubility of the target sulfinated substance not only improves the yield thereof and the efficiency of an isolation operation but also makes the inorganic impurities, e.g., the residual bromine in particular, readily removable, which is a further effect obtained by using the organic base in the present invention.

As discussed above, the target ammonium sulfinate is obtained by conducting extraction (for example, with the organic solvent), rinsing an organic layer with water and a sodium thiosulfate aqueous solution (or a sodium sulfite aqueous solution) or the like, and then distilling the solvent out of the organic layer. In some cases, the target ammonium sulfinate may be purified by recrystallization or the like.

[$2^{nd}$ Step: Oxidation Step]

Then, a $2^{nd}$ step of the present invention will be discussed. The $2^{nd}$ step is a step of reacting the ammonium hydroxyfluoroalkanesulfinate [2] with an oxidizing agent thereby obtaining an ammonium hydroxyfluoroalkanesulfonate represented by the general formula [3] (i.e., an oxidation step).

The oxidizing agent used in this step is exemplified by m-chloroperbenzoic acid, t-butyl hydroperoxide, potassium peroxydisulfate, potassium permanganate, sodium perborate, m-sodium iodate, chromic acid, sodium dichromate, halogen, iodobenzene dichloride, iodobenzene diacetate, osmium (VIII) oxide, ruthenium(VIII) oxide, sodium hypochlorite, sodium chlorite, oxide gas and ozone gas, in addition to hydrogen peroxide. Preferable ones are hydrogen peroxide, m-chloroperbenzoic acid and t-butyl hydroperoxide and the like.

The mole ratio of the oxidizing agent to the ammonium hydroxyfluoroalkanesulfinate [2] is usually 0.9 to 10.0, preferably 1.0 to 2.0. In a case where the raw material ammonium sulfinate is such a crude substance as to be unclear in exact number of moles, it is required only to add the oxidizing agent relative to the molar amount of the bromofluoroalcohol prepared before sulfination and represented by the general formula [1].

Furthermore, the oxidizing agent can be used also in combination with a transition metal catalyst. Examples of the transition metal catalyst are disodium tungstate, iron(III) chloride, ruthenium(III) chloride and selenium(IV) oxide, and preferably disodium tungstate.

The mole ratio of the transition metal catalyst to the ammonium hydroxyfluoroalkanesulfinate [2] is usually 0.0001 to 1.0, preferably 0.001 to 0.5 and more preferably 0.001 to 0.1.

Moreover, in addition to the oxidizing agent and the transition metal catalyst, a buffering agent may be used for the purpose of adjusting the pH of a reaction liquid. Examples of the buffering agent include disodium hydrogenphosphate, sodium dihydrogenphosphate, dipotassium hydrogenphosphate and potassium dihydrogenphosphate. The mole ratio of the buffering agent to the ammonium hydroxyfluoroalkanesulfinate [2] is usually 0.01 to 2.0, preferably 0.03 to 1.0 and more preferably 0.05 to 0.5.

This reaction is usually conducted in a reaction solvent. It is preferable that the reaction solvent is an organic solvent such as lower alcohols, tetrahydrofuran, N,N-dimethylformamide, N,N-dimethylacetamide, acetonitrile, dimethyl sulfoxide, acetic acid and trifluoroacetic acid, in addition to water. The more preferable ones are water, methanol, N,N-dimethylacetamide, acetonitrile and dimethyl sulfoxide, and the particularly preferable ones are water and methanol.

Additionally, the organic solvent may be used in combination with water, as necessary. In this case, the ratio of the organic solvent to be used is usually not less than 5 parts by weight, preferably not less than 10 parts by weight and more preferably 20 to 90 parts by weight relative to 100 parts by weight of total of the organic solvent and water. The amount of the reaction solvent to be used is usually 1 to 100 parts by weight, preferably from 2 to 100 parts by weight and more preferably 5 to 50 parts by weight relative to 1 part by weight of the ammonium hydroxyfluoroalkanesulfinate [2].

The reaction temperature is usually 0 to 100° C., preferably 5 to 60° C. and more preferably 5 to 40° C. The reaction time is usually 0.1 to 72 hours, preferably 0.5 to 24 hours and more preferably 0.5 to 12 hours; however, it is further preferable to determine a temporal point at which the raw material ammonium hydroxyfluoroalkanesulfinate [2] has been consumed as the endpoint of the reaction, by using an analytical device such as thin layer chromatography (TLC) and nuclear magnetic resonance (NMR).

Then, there will be discussed a treatment conducted after the reaction. In the above-discussed 1$^{st}$ step, fat-solubility of the obtained ammonium hydroxyfluoroalkanesulfonate is improved by using amines as the base. As a result, it becomes possible to dissolve the fat-soluble ammonium hydroxyfluoroalkanesulfonate in the organic solvent by treating an unpurified crude product which contains a great amount of inorganic impurities and obtained upon the reaction and an aftertreatment, with the organic solvent. At this time, the inorganic impurities contrarily having no fat-solubility can be precipitated and then filtered away. Examples of such a solvent include: halogen-based solvents such as chloroform and dichloromethane; ether-based solvents such as diethyl ether, diisopropyl ether and tert-butyl methyl ether; acetic ester-based solvents such as ethyl acetate and butyl acetate; and ketone-based solvents such as acetone and 2-butanone.

With such a treatment, it becomes possible to increase the purity of a target ammonium hydroxyfluoroalkanesulfonate (see Example 1, Example 2 and Comparative Example 3).

In some cases, the obtained ammonium hydroxyfluoroalkanesulfonate [3] may be purified by recrystallization or the like.

[3$^{rd}$ Step: Esterification Step]

Then a 3$^{rd}$ step of the present invention will be discussed. The 3$^{rd}$ step is a step of esterifying the ammonium hydroxyfluoroalkanesulfonate represented by the general formula [3] and obtained by the 2$^{nd}$ step through a reaction with a carboxylic acid derivative represented by the general formula [6] or general formula [7] thereby producing an ammonium fluoroalkanesulfonate represented by the general formula [4].

[6]

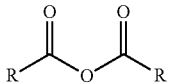

[7]

In the general formula [6], X' represents a hydroxyl group or a halogen. The halogen is exemplified by fluorine, chlorine, bromine and iodine, in which chlorine is particularly preferable.

In the general formula [6] of the general formula [7], R represents a linear or branched alkyl group having 1 to 10 carbon atoms, a linear or branched alkenyl group having 1 to 10 carbon atoms and a polymerizable double bond at least at the end moiety, an alicyclic organic group having 3 to 20 carbon atoms, an organic group having 3 to 20 carbon atoms and containing an alicyclic organic group and a linear alkylene group, a monocyclic or polycyclic lactone having 3 to 30 carbon atoms, or an aryl group having 6 to 20 carbon atoms. (In this formula, some or all of hydrogen atoms disposed in the alkyl group, the alkenyl group, the alicyclic organic group, the organic group containing the alicyclic organic group and the linear alkylene group, the monocyclic or polycyclic lactone or the aryl group may be substituted with fluorine, a hydroxyl group, a hydroxycarbonyl group, or a linear, branched or cyclic alkoxy group having 1 to 6 carbon atoms. Additionally, two hydrogen atoms disposed on the same carbon that constructs the alkyl group, the alkenyl group, the alicyclic organic group, or the organic group containing the alicyclic organic group and the linear alkylene group may be substituted with one oxygen atom to form a keto group. Furthermore, one of hydrogen atoms disposed on the alkyl group may be substituted with 2-acryloyloxy group, a 2-methacryloyloxy group or a trifluoromethyl methacryloyloxy group.))

Concrete examples of R are discussed as below.

The linear or branched alkyl group having 1 to 10 carbon atoms can be exemplified by methyl group, ethyl group, n-propyl group, i-propyl group, n-butyl group, t-butyl group, n-pentyl group, n-hexyl group, n-heptyl group, n-octyl group, n-nonyl group and n-decyl group, for example.

The linear or branched alkenyl group of 1 to 10 carbon atoms having a polymerizable double bond at least at the end moiety can be exemplified by vinyl group, 1-methylethenyl group, allyl group, 3-butenyl group, 1-methylallyl group, 2-methylallyl group, 4-pentenyl group and 5-hexenyl group, for example.

The alicyclic organic group having 3 to 20 carbon atoms can be exemplified by cyclopentyl group, cyclohexyl group, adamantyl group, norbornyl group, camphoroyl group, cyclopentylmethyl group, cyclopentylethyl group, cyclohexylmethyl group, cyclohexylethyl group, adamantylmethyl group, adamantylethyl group, norbornylmethyl group, norbornylethyl group, camphoroylmethyl group and camphoroylethyl group, for example.

The organic group having 3 to 20 carbon atoms and containing the alicyclic organic group and the linear alkylene group means "an organic group to which one valence of the alicyclic organic group and one valence of the linear alkylene group are bonded". Concrete examples thereof include cyclopropylmethyl group, cyclobutylmethyl group, cyclopentylmethyl group, cyclohexylmethyl group, bornylmethyl group, norbornylmethyl group and adamantylmethyl group, for example. The number of carbon atoms of the linear alkylene group is not particularly limited; however, it is 1 to 6, for example.

The monocyclic or polycyclic lactone having 3 to 30 carbon atoms can be exemplified by γ-butyrolactone, γ-valerolactone, angelica lactone, γ-hexylactone, γ-heptalactone, γ-octalactone, γ-nonalactone, 3-methyl-4-octanolyde (whisky lactone), γ-decalactone, γ-undecalactone, γ-dodecalactone, γ-jasmolactone (7-decenolactone), δ-hexylactone, 4,6,6(4,4,6)-trimethyltetrahydropyran-2-one, δ-octalactone, δ-nonalactone, δ-decalactone, δ-2-decenolactone, δ-undecalactone, δ-dodecalactone, δ-tridecalactone, δ-tetradecalactone, lactoscaton, ε-decalactone, ε-dodecalactone, cyclohexyllactone, jasmine lactone, cis-jasmone lactone, methyl γ-decalactone and the followings, for example.

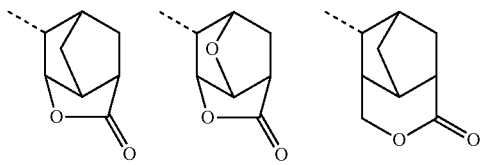

(DOTTED LINES REPRESENT BONDING LOCATIONS)

The aryl group having 6 to 20 carbon atoms can be exemplified by phenyl group, o-tolyl group, m-tolyl group, p-tolyl group, p-hydroxyphenyl group, 1-naphthyl group, 1-anthracenyl group and benzyl group, for example.

Incidentally, some or all of hydrogen atoms disposed in the alkyl group, the alkenyl group, the alicyclic organic group, the organic group having the alicyclic organic group and the linear alkylene group, the monocyclic or polycyclic lactone or the aryl group may be substituted with fluorine, a hydroxyl group, a hydroxycarbonyl group, or a linear, branched or cyclic alkoxy group having 1 to 6 carbon atoms, as discussed above. Additionally, two hydrogen atoms disposed on the same carbon that constructs the alkyl group, the alkenyl group, the alicyclic organic group, or the organic group having the alicyclic organic group and the linear alkylene group may be substituted with one oxygen atom to form a keto group. Furthermore, one of hydrogen atoms disposed on the alkyl group may be substituted with 2-acryloyloxy group or 2-methacryloyloxy group.

As discussed above, it is possible to use an acyl group having a polymerizable double bond, i.e., an unconjugated unsaturated moiety (a double or triple bond), which is the principal feature.

A method for esterification can be exemplified by: a method of dehydrating and condensing a carboxylic acid represented by the general formula [6] (X'=OH) and the ammonium hydroxyfluoroalkanesulfonate [3] in the presence of an acid catalyst (Fischer esterification); and a method of reacting a carboxylic acid halide (X'=Cl, Br, I, F) represented by the general formula [6] or a carboxylic acid anhydride represented by the general formula [7] with the ammonium hydroxyfluoroalkanesulfonate [3].

When using the carboxylic acid represented by the general formula [6] (X'=OH), the used amount of the carboxylic acid which is to act on the ammonium hydroxyfluoroalkanesulfonate [3] is usually 0.1 to 5 moles, preferably 0.2 to 3 moles and more preferably 0.5 to 2 moles relative to 1 mole of the ammonium hydroxyfluoroalkanesulfonate [3], though not particularly limited. It is particularly preferable that the amount of the carboxylic acid to be used is in an amount of 0.8 to 1.5 moles.

In the reaction, an aprotic solvent such as dichloroethane, toluene, ethylbenzene, monochlorobenzene, acetonitrile and N,N-dimethylformamide is usually used. These solvents may be used singly or in combination of not less than two kinds thereof.

The reaction temperature is not particularly limited; however, it is usually within a range of 0 to 200° C., preferably 20 to 180° C. and more preferably 50 to 150° C. It is preferable to conduct the reaction with stirring.

The reaction time usually ranges from several minutes to 100 hours, preferably from 30 minutes to 50 hours and more preferably from 1 to 20 hours, though it depends also on the reaction temperature; however, it is preferable to determine a temporal point at which the raw material ammonium hydroxyfluoroalkanesulfonate [3] has been consumed as the endpoint of the reaction, by using an analytical device such as nuclear magnetic resonance (NMR).

Usually, this reaction is conducted with the addition of an organic acid such as p-toluenesulfonic acid and/or an inorganic acid such as sulfuric acid, as an acid catalyst. Alternatively, 1,1'-carbonyldiimidazole, N,N'-dicyclohexylcarbodiimide or the like may be added as a dehydrating agent. The amount of the acid catalyst to be used is not particularly limited but preferably 0.0001 to 10 moles, preferably 0.001 to 5 moles and more preferably 0.01 to 1.5 moles relative to 1 mole of the ammonium hydroxyfluoroalkanesulfonate [3].

It is preferable to conduct esterification reaction using the acid catalyst while carrying out dehydration, for example, by using a Dean-Stark apparatus, since the reaction time tends to be shortened thereby.

By taking usual means such as extraction, distillation, recrystallization or the like after termination of the reaction, it becomes possible to obtain the ammonium fluoroalkanesulfonate represented by the general formula [4]. Moreover, it can be purified by column chromatography, recrystallization or the like as necessary.

On the other hand, in the case of using the carboxylic acid halide (X'=Cl, Br, I, F) represented by the general formula [6] or the carboxylic acid anhydride represented by the general formula [7], the used amount of the carboxylic acid halide (X'=Cl, Br, I, F) represented by the general formula [6] or the carboxylic acid anhydride represented by the general formula [7] which is to act on the ammonium hydroxyfluoroalkanesulfonate [3] is usually 0.1 to 5 moles, preferably 0.2 to 3 moles and more preferably 0.5 to 2 moles relative to 1 mole of the ammonium hydroxyfluoroalkanesulfonate [3], though not particularly limited. It is particularly preferable that the used amount of the carboxylic acid halide or the carboxylic acid anhydride is 0.8 to 1.5 moles.

The reaction may be conducted in the absence of solvents or in a solvent non-reactive with the reaction. Such solvents are required only to be non-reactive one and therefore not particularly limited. However, hydrocarbon-based nonpolar solvents such as n-hexane, benzene and toluene are not preferable as the solvent used in this step because the ammonium hydroxyfluoroalkanesulfonate [3] is hardly dissolved in these solvents. The preferable examples thereof are: water; ketone-based solvents such as acetone, methyl ethyl ketone and methyl isobutyl ketone; ester-based solvents such as ethyl acetate and butyl acetate; ether-based solvents such as diethyl ether, diethylene glycol dimethyl ether, tetrahydrofuran and dioxane; halogen-based solvents such as dichloromethane, chloroform, carbon tetrachloride, 1,2-dichloroethane, tetrachloroethylene, chlorobenzene and ortho-chlorobenzene;

and polar solvents such as acetonitrile, N,N-dimethylformamide, N,N-dimethylimidazolidinone, dimethyl sulfoxide and sulfolane. These solvents may be used singly or in combination of not less than two kinds thereof.

The reaction temperature is not particularly limited and usually within a range of −78 to 150° C., preferably −20 to 120° C. and more preferably 0 to 100° C.

The reaction time is usually several minutes to 100 hours, preferably 30 minutes to 50 hours and more preferably 1 to 20 hours, though it depends also on the reaction temperature; however, it is further preferable to determine a temporal point at which the raw material ammonium hydroxyfluoroalkanesulfonate [3] has been consumed as the endpoint of the reaction, by using an analytical device such as nuclear magnetic resonance (NMR).

In the case of using the carboxylic acid halide represented by the general formula [6], the reaction may be conducted while removing a by-product hydrogen halide (e.g., hydrogen chloride or the like) from the reaction system in the absence of catalysts, or may be conducted in the use of a dehydrohalogenating agent (an acid acceptor). In the case of using the carboxylic acid anhydride represented by the general formula [7], the acid acceptor for receiving by-product acids may be used.

Examples of the acid acceptor include: organic bases such as triethylamine, pyridine, picoline, dimethylaniline, diethylaniline, 1,4-diazabicyclo [2.2.2]octane (DABCO) and 1,8-diazabicyclo [5.4.0]undec-7-ene (DBU); and inorganic bases such as sodium hydrogencarbonate, sodium carbonate, potassium carbonate, lithium carbonate, sodium hydroxide, potassium hydroxide, calcium hydroxide and magnesium oxide. The amount of the acid acceptor to be used is not particularly limited but preferably ranges from 0.05 to 10 moles, preferably from 0.1 to 5 moles and more preferably from 0.5 to 3 moles relative to 1 mole of the ammonium hydroxyfluoroalkanesulfonate [3].

By taking usual means such as extraction, recrystallization or the like after termination of the reaction, it becomes possible to obtain the ammonium fluoroalkanesulfonate represented by the general formula [4]. Moreover, it can be purified by column chromatography, recrystallization or the like as necessary.

[4$^{th}$ Step: Onium Salt-Exchanging Step]

Then, a 4$^{th}$ step of the present invention will be discussed. The 4$^{th}$ step is a step of performing an onium salt-exchange by using a monovalent onium salt represented by the general formula [8]

$$Q^+X^- \qquad [8]$$

on the ammonium fluoroalkanesulfonate represented by the general formula [4] and obtained by the 3$^{rd}$ step, thereby obtaining an onium fluoroalkanesulfonate represented by the general formula [5] (an onium salt-exchanging step).

An onium cation $Q^+$ contained in the general formula [8] represents a sulfonium cation shown in the following general formula (a) or the following general formula (b), or an iodonium cation shown in the following general formula (c).

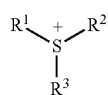

In the general formula (a), $R^1$, $R^2$ and $R^3$ mutually independently represent a substituted or unsubstituted linear or branched alkyl group, alkenyl group or oxoalkyl group having 1 to 10 carbon atoms, or a substituted or unsubstituted aryl group, aralkyl group or aryloxoalkyl group having 6 to 18 carbon atoms. Alternatively, two or more of $R^1$, $R^2$ and $R^3$ may bond to each other to form a ring together with a sulfur atom shown in the formula.

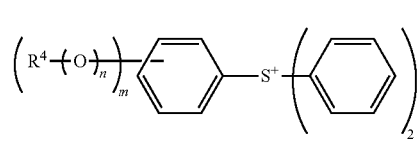

In the general formula (b), $R^4$ represents a substituted or unsubstituted linear, branched or cyclic alkyl group or alkenyl group having 1 to 20 carbon atoms, or a substituted or unsubstituted aryl group having 6 to 14 carbon atoms. m represents an integer of 1 to 5, and n represents 0 (zero) or 1.

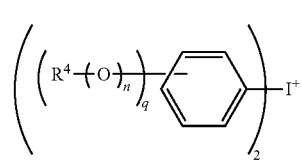

In the general formula (c), $R^4$ represents a substituted or unsubstituted linear, branched or cyclic alkyl group or alkenyl group having 1 to 20 carbon atoms, or a substituted or unsubstituted aryl group having 6 to 14 carbon atoms. q represents an integer of 0 (zero) to 5, and n represents 0 (zero) or 1.

Hereinafter, a sulfonium cation represented by the general formula (a) or the general formula (b) and an iodonium cation represented by the general formula (c) will be discussed in detail.

Sulfonium Cation Represented by the General Formula (a)

Concrete examples of $R^1$, $R^2$ or $R^3$ as shown in the general formula (a) are as follows. Examples of alkyl group include methyl group, ethyl group, n-propyl group, isopropyl group, cyclopropyl group, n-butyl group, sec-butyl group, isobutyl group, tert-butyl group, n-pentyl group, cyclopentyl group, n-hexyl group, n-heptyl group, 2-ethylhexyl group, cyclohexyl group, cycloheptyl group, 4-methylcyclohexyl group, cyclohexylmethyl group, n-octyl group, n-decyl group, 1-adamantyl group, 2-adamantyl group, bicyclo[2.2.1]hepten-2-yl group, 1-adamantanemethyl group and 2-adamantanemethyl group. Examples of alkenyl group include vinyl group, allyl group, propenyl group, butenyl group, hexenyl group and cyclohexenyl group. Examples of oxoalkyl group include 2-oxocyclopentyl group, 2-oxocyclohexyl group, 2-oxopropyl group, 2-oxoethyl group, 2-cyclopentyl-2-oxoethyl group, 2-cyclohexyl-2-oxoethyl group and 2-(4-methylcyclohexyl)-2-oxoethyl group. Examples of aryl group are: phenyl group; naphthyl group; thienyl group; alkoxy phenyl groups such as p-methoxyphenyl group, m-methoxyphenyl group, o-methoxyphenyl group, p-ethoxyphenyl group, p-tert-butoxyphenyl group and m-tert-butoxyphenyl group; alkyl phenyl group such as 2-methylphenyl group, 3-methylphenyl group, 4-methylphenyl group and ethylphenyl group; alkyl naphthyl group such as methyl naphthyl group and ethyl naphthyl group; dialkyl naphthyl group such as diethyl naphthyl group; dialkoxy naphthyl group such as dimethoxy naphthyl group and diethoxy naphthyl group.

Examples of aralkyl group include benzyl group, 1-phenylethyl group and 2-phenylethyl group. Examples of aryloxoalkyl group include 2-aryl-2-oxoethyl group such as 2-phenyl-2-oxoethyl group, 2-(1-naphthyl)-2-oxoethyl group and 2-(2-naphthyl)-2-oxoethyl group. Additionally, in the case where two or more of $R^1$, $R^2$ and $R^3$ bond to each other through a sulfur atom to form a cyclic structure, the examples include 1,4-butylene and 3-oxa-1,5-pentylene. Furthermore, examples of substituent are aryl groups having a polymerizable substituent such as acryloyloxy group and methacryloyloxy group as the substituent. Concrete examples thereof are 4-(acryloyloxy)phenyl group, 4-(methacryloyloxy)phenyl group, 4-vinyloxyphenyl group and 4-vinylphenyl group.

Further concrete examples of the sulfonium cation represented by the general formula (a) include triphenylsulfonium, (4-tert-butylphenyl)diphenylsulfonium, bis(4-tert-butylphenyl)phenylsulfonium, tris(4-tert-butylphenyl)sulfonium, (3-tert-butylphenyl)diphenylsulfonium, bis(3-tert-butylphenyl)phenylsulfonium, tris(3-tert-butylphenyl)sulfonium, (3,4-ditert-butylphenyl)diphenylsulfonium, bis(3,4-ditert-butylphenyl)phenylsulfonium, tris(3,4-ditert-butylphenyl)sulfonium, (4-tert-butoxyphenyl)diphenylsulfonium, bis(4-tert-butoxyphenyl)phenylsulfonium, tris(4-tert-butoxyphenyl)sulfonium, (3-tert-butoxyphenyl)diphenylsulfonium, bis(3-tert-butoxyphenyl)phenylsulfonium, tris(3-tert-butoxyphenyl)sulfonium, (3,4-ditert-butoxyphenyl)diphenylsulfonium, bis(3,4-ditert-butoxyphenyl)phenylsulfonium, tris(3,4-ditert-butoxyphenyl)sulfonium, diphenyl(4-thiophenoxyphenyl)sulfonium, (4-tert-butoxycarbonylmethyloxyphenyl)diphenylsulfonium, tris(4-tert-butoxycarbonylmethyloxyphenyl)diphenylsulfonium, (4-tert-butoxyphenyl)bis(4-dimethylaminophenyl)sulfonium, tris(4-dimethylaminophenyl)sulfonium, 2-naphthyldiphenylsulfonium, dimethyl(2-naphthyl)sulfonium, (4-hydroxyphenyl)dimethylsulfonium, (4-methoxyphenyl)dimethylsulfonium, trimethylsulfonium, (2-oxocyclohexyl)cyclohexylmethylsulfonium, trinaphthylsulfonium, tribenzylsulfonium, diphenylmethylsulfonium, dimethylphenylsulfonium, 2-oxo-2-phenylethylthiacyclopentanium, diphenyl-2-thienylsulfonium, 4-n-butoxynaphthyl-1-thiacyclopentanium, 2-n-butoxynaphthyl-1-thiacyclopentanium, 4-methoxynaphthyl-1-thiacyclopentanium, and 2-methoxynaphthyl-1-thiacyclopentanium. More preferable examples are triphenylsulfonium, (4-tert-butylphenyl)diphenylsulfonium, (4-tert-butoxyphenyl)diphenylsulfonium, tris(4-tert-butylphenyl)sulfonium and (4-tert-butoxycarbonylmethyloxyphenyl)diphenylsulfonium.

Still further examples thereof are 4-(methacryloyloxy)phenyldiphenylsulfonium, 4-(acryloyloxy)phenyldiphenylsulfonium, 4-(methacryloyloxy)phenyldimethylsulfonium, and 4-(acryloyloxy)phenyldimethylsulfonium. Regarding these polymerizable sulfonium cations, Japanese Patent Application Publication No. 4-230645, Japanese Patent Application Publication 2005-84365 and the like can be referred to.

Sulfonium Cation Represented by the General Formula (b)

In the general formula (b), the location of $R^4$—$(O)_n$— group as a substituent is not particularly limited, but preferably occupies position 4 or 3, more preferably position 4 of phenyl group. In the formula, n represents 0 (zero) or 1. Concrete examples of $R^4$ include methyl group, ethyl group, n-propyl group, see-propyl group, cyclopropyl group, n-butyl group, sec butyl group, isobutyl group, tort-butyl group, n-pentyl group, cyclopentyl group, n-hexyl group, cyclohexyl group, n-octyl group, n-decyl group, n-dodecyl group, 1-adamantyl group, 2-adamantyl group, bicyclo[2.2.1]hepten-2-yl group, phenyl group, 4-methoxyphenyl group, 4-tert-butylphenyl group, 4-biphenyl group, 1-naphthyl group, 2-naphthyl group, 10-anthranyl group and 2-furanyl group. Additionally, in the case of n=1, the examples further include acryloyl group, methacryloyl group, vinyl group and allyl group.

Concrete examples of the sulfonium cation are (4-methylphenyl)diphenylsulfonium, (4-ethylphenyl)diphenylsulfonium, (4-cyclohexylphenyl)diphenylsulfonium, (4-n-hexylphenyl)diphenylsulfonium, (4-n-octyl)phenyldiphenylsulfonium, (4-methoxyphenyl)diphenylsulfonium, (4-ethoxyphenyl)diphenylsulfonium, (4-tort-butoxyphenyl)diphenylsulfonium, (4-cyclohexyloxyphenyl)diphenylsulfonium, (4-trifluoromethylphenyl)diphenylsulfonium, (4-trifluoromethyloxyphenyl)diphenylsulfonium, and (4-tert-butoxycarbonylmethyloxyphenyl)diphenylsulfonium.

Iodonium Cation Represented by the General Formula (c)

In the general formula (c), the location of $R^4$—$(O)_n$— group as a substituent is not particularly limited, but preferably occupies position 4 or 3 and more preferably the position 4 of phenyl group. In the formula, n is 0 (zero) or 1. Concrete examples of $R^4$ are the same as those discussed for the above general formula (b).

Concrete examples of the iodonium cation include diphenyliodonium, bis(4-methylphenyl)iodonium, bis(4-ethylphenyl)iodonium, bis(4-tert-butylphenyl)iodonium, bis(4-(1,1-dimethylpropyl)phenyl)iodonium, (4-methoxyphenyl)phenyliodonium, (4-tert-butoxyphenyl)phenyliodonium, (4-acryloyloxy)phenylphenyliodonium, and (4-methacryloyloxy)phenylphenyliodonium. Among these, bis(4-tert-butylphenyl)iodonium is preferably used.

Then, examples of the monovalent anion $X^-$ shown in the general formula [8] include $F^-$, $Cl^-$, $Br^-$, $I^-$, $ClO_4^-$, $HSO_4^-$, $H_2PO_4^-$, $BF_4^-$, $PF_6^-$, $SbF_6^-$, aliphatic sulfonic acid anion, aromatic sulfonic acid anion, trifluoromethanesulfonic acid anion, fluorosulfonic acid anion, aliphatic carboxylic acid anion, aromatic carboxylic acid anion, fluorocarboxylic acid anion and trifluoroacetic acid anion. The preferable ones are $Cl^-$, $Br^-$, $HSO_4^-$, $BF_4^-$, aliphatic sulfonic acid ion and the like. The more preferable ones are $Cl^-$, Br. and $HSO_4^-$.

The mole ratio of the monovalent onium salt represented by the general formula [8] to the ammonium fluoroalkanesulfonate [4] is usually 0.5 to 10.0, preferably 0.8 to 2.0 and more preferably 0.9 to 1.2.

This reaction is usually conducted in a reaction solvent. Preferable examples of the reaction solvent are organic solvents such as lower alcohols, tetrahydrofuran, N,N-dimethylformamide, N,N-dimethylacetamide, acetonitrile and dimethyl sulfoxide, in addition to water. The more preferable ones are water, methanol, N,N-dimethylacetamide, acetonitrile and dimethyl sulfoxide. The particularly preferable one is water.

Additionally, the organic solvent may be used in combination with water, as necessary, in which case the ratio of the organic solvent to be used is usually not less than 5 parts by weight, preferably not less than 10 parts by weight and more preferably 20 to 90 parts by weight relative to 100 parts by weight of total of the organic solvent and water. The amount of the reaction solvent to be used is usually 1 to 100 parts by weight, preferably 2 to 100 parts by weight and more preferably 5 to 50 parts by weight relative to 1 part by weight of a counter ion exchange precursor.

The reaction temperature is usually 0 to 80° C. and preferably 5 to 30° C. The reaction time is usually 10 minutes to 16 hours, preferably 30 minutes to 6 hours; however, it is further preferable to determine a temporal point at which the raw material ammonium fluoroalkanesulronate [4] has been consumed as the endpoint of the reaction, by using an analytical device such as thin layer chromatography (TLC) and nuclear magnetic resonance (NMR).

The thus obtained onium fluoroalkanesulfonate represented by the general formula [5] can be rinsed with an organic solvent or can be extracted to be purified, as necessary. Examples of the organic solvent are preferably those who are not to be mixed with water, such as: esters including ethyl acetate, n-butyl acetate and the like; ethers including diethyl ether and the like; and halogenated alkyls including methylene chloride, chloroform and the like.

By the method as had been discussed, it is possible to produce either of an onium fluoroalkanesulfonate not having in its structure an unconjugated unsaturated moiety (a double or triple bond) as a substituent for acyl group and an onium fluoroalkanesulfonate having the unconjugated unsaturated moiety. This compound can be provided as a photoacid generator used for a chemically amplified resist material.

By the way, the $3^{rd}$ step and the $4^{th}$ step of the present invention can be replaced with each other in order (Equation [4]).

Namely, it involves a step of carrying out an onium-salt exchange on the ammonium hydroxyfluoroalkanesulfonate represented by the general formula [3] thereby obtaining an onium hydroxyfluoroalkanesulfonate represented by the general formula [11] (a $3'^{rd}$ step: an onium salt-exchanging step); and a step of esterifying it through a reaction with a carboxylic acid derivative represented by the general formula [6] or general formula [7] (a $4'^{th}$ step: an esterification step) thereby producing the onium fluoroalkanesulfonate represented by the general formula [5].

However, in this method, the onium hydroxyfluoroalkanesulfinate is produced prior to the esterification step. The onium sulfonate has photosensitivity and therefore must be handled under a light-tight condition, as discussed above. Accordingly, this method requires a step performed under the light-tight condition at two different times, so that facilities therefor become a considerable burden.

EQUATION [4]

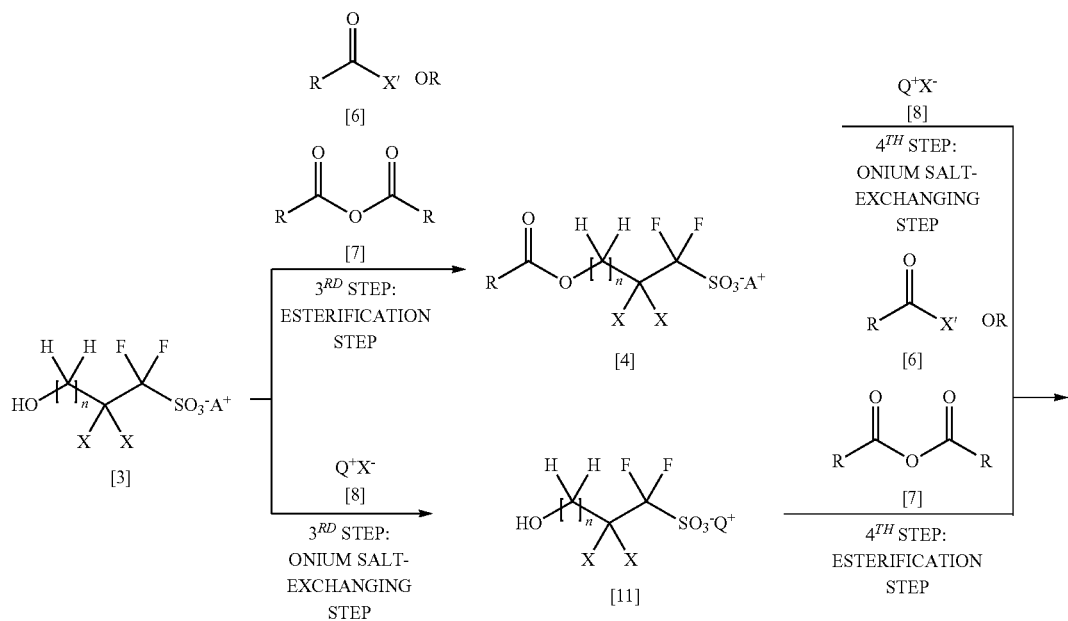

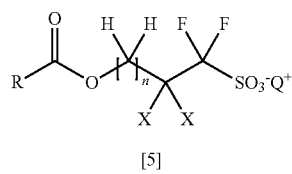

Accordingly, the method is preferably conducted by reversing the order of the 3$^{rd}$ step and the 4$^{th}$ step of the present invention.

EXAMPLES

The present invention will be more specifically discussed with reference to the following Examples; however, the present invention is not limited by these Examples.

Example 1-1

Synthesis of triethylammonium 1,1-difluoro-2-hydroxy-ethane-1-sulfinate

1$^{st}$ Step: Sulfination Step

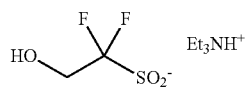

A 100 mL reactor was charged with 5.0 g (0.029 mole/1.0 equivalent) of 2-bromo-2,2-difluoroethan-1-ol, 14.0 g of acetonitrile, 12.5 g of water, 8.1 g (0.047 mole/1.6 equivalents) of sodium dithionite and 5.3 g (0.052 mole/1.8 equivalents) of triethylamine, followed by 4 hours of stirring at 70° C.

Upon confirming the termination of the reaction, the reaction liquid underwent cooling and 30 mL of a 1N hydrochloric acid solution was added thereto, followed by stirring. Then, the solvent was distilled out of the reaction liquid, thereby obtaining 23.0 g of a target triethylammonium 1,1-difluoro-2-hydroxy-ethane-1-sulfinate. It exhibited a purity of 26% and a yield of 83% at this time.

An obtained crude product was added in an amount of 10.0 g (26% purity, 2.6 g content, 0.011 mole/1.0 equivalent) to 50 mL of acetone, followed by 1 hour of stirring at room temperature. Thereafter, filtration was performed in the use of a filter paper. An obtained filtrate was concentrated and dried, thereby obtaining 2.69 g of a target triethylammonium 1,1-difluoro-2-hydroxy-ethane-1-sulfinate. It exhibited a purity of 91%, a content of 2.45 g or 0.0099 mole and a yield of 94% at this time.

As a result of [Example 1-1], it was found that an ammonium salt could be obtained with high yields by the addition of amine such as triethylammonium. Accordingly, particularly in a case where n of the general formula [1] of the present invention is 0, it is apparent that the addition of amine provides such an advantage effect that the ammonium salt can be obtained with high yields as compared with a method of obtaining a sodium salt without adding amine (see Comparative Example 1).

Properties of triethylammonium 1,1-difluoro-2-hydroxy-ethane-1-sulfinate $^{1}$H NMR (Solvent for measurement: Deuterated dimethyl sulfoxide, Reference material: Tetramethylsilane); δ=3.80 (t, 2H), 3.01 (q, 6H), 1.17 (t, 9H)

$^{19}$F NMR (Solvent for measurement: Deuterated dimethyl sulfoxide, Reference material: Trichlorofluoromethane); δ=−121.0 (s, 2F)

Example 1-2

Synthesis of triethylammonium 1,1-difluoro-2-hydroxy-ethane-1-sulfonate

2$^{nd}$ Step: Oxidation Step

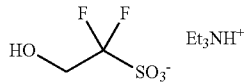

A 100 mL reactor was charged with 11.5 g (26% purity, 0.012 mole/1.0 equivalent) of triethylammonium 1,1-difluoro-2-hydroxy-ethane-1-sulfinate, 20 g of water and 4.2 g (0.036 mole/3.0 equivalents) of 30% hydrogen peroxide at room temperature, followed by one day of stirring at 40° C. Upon confirming the termination of the reaction, the reaction liquid underwent cooling. Thereafter, the reaction liquid was subjected to distillation of the solvent and brought into dryness, thereby obtaining 10.5 g of a target triethylammonium 1,1-difluoro-2-hydroxy-ethane-1-sulfonate. It exhibited a purity of 26% and a yield of 85% at this time.

An obtained crude product was added in an amount of 10.0 g (26% purity, 2.6 g content, 9.87 millimoles/1.0 equivalent) to 50 mL of acetone, followed by 1 hour of stirring at room temperature. Thereafter, filteration was performed in the use of a filter paper. An obtained filtrate was concentrated and dried, thereby obtaining 2.49 g of a target triethylammonium 1,1-difluoro-2-hydroxy-ethane-1-sulfonate. It exhibited a purity of 94%, a content of 2.34 g or 8.88 millimoles and a yield of 90% at this time.

Properties of triethylammonium 1,1-difluoro-2-hydroxy-ethane-1-sulfonate $^{1}$H NMR (Solvent for measurement: Deuterated dimethyl sulfoxide, Reference material: Tetramethylsilane); δ=3.84 (t, 2H), 3.04 (q, 6H), 1.18 (t, 9H)

$^{19}$F NMR (Solvent for measurement: Deuterated dimethyl sulfoxide, Reference material: Trichlorofluoromethane); δ=−115.6 (s, 2F)

Example 1-3

Synthesis of triethylammonium 1,1-difluoro-2-(2-methyl-acryloyloxy)-ethane-1-sulfonate 3$^{rd}$ Step: Esterification Step

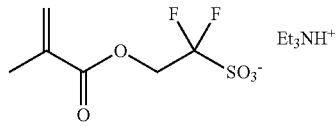

A 100 mL reactor was charged with 2.49 g (94% purity, 8.88 millimoles/1.0 equivalent) of triethylammonium 1,1-difluoro-2-hydroxy-ethane-1-sulfonate, 20.0 g of acetonitrile, 5.46 g (35.5 millimoles/4.0 equivalent) of methacrylic anhydride, 5.22 g (51.5 millimoles/5.8 equivalents) of triethylamine and 0.03 g of nonflex MBP (2,2'-methylene-bis (4-methyl-6-tert-butylphenol)), followed by 3 hours of stirring at 50° C. The reaction liquid underwent cooling and then 25 g of water was added thereto, followed by 30 minutes of stirring. Then, a volatile component was distilled out of the reaction liquid under a reduced pressure. An obtained liquid was rinsed with 20 g of diisopropyl ether three times and then an organic layer was separated therefrom, thereby obtaining a target triethylammonium 1,1-difluoro-2-(2-methyl-acryloyloxy)-ethane-1-sulfonate in the form of an aqueous solution. An obtained target compound was brought into the next step without purification.

Example 1-4

Synthesis of triphenylsulfonium 1,1-difluoro-2-(2-methyl-acryloyloxy)-ethane-1-sulfonate 4$^{th}$ Step: Onium Salt-Exchanging Step

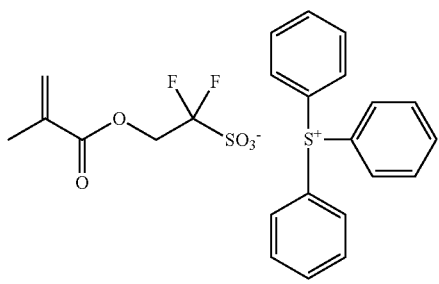

A 50 mL reactor was charged with the triethylammonium 1,1-difluoro-2-(2-methyl-acryloyloxy)-ethane-1-sulfonate aqueous solution obtained by the 3$^{rd}$ step, and a solution of 3.18 g (8.9 millimoles) of triphenylsulfonium bromide and 20 g of chloroform, followed by 3 hours of stirring at room temperature. Subsequently, an organic layer was separated, and the thus obtained organic layer was rinsed with 20 g of water four times. Subsequently, it was rinsed with 20 g of diisopropyl ether three times and then a volatile component was distilled off, thereby obtaining 3.92 g of a target triphenylsulfonium 1,1-difluoro-2-(2-methyl-acryloyloxy)-ethane-1-sulfonate. It exhibited a purity of 97% at this time, and a yield of 87% taken over from the 3$^{rd}$ step.

Properties of triphenylsulfonium 1,1-difluoro-2-(2-methyl-acryloyloxy)-ethane-1-sulfonate $^1$H NMR (Solvent for measurement: Deuterated dimethyl sulfoxide, Reference material: Tetramethylsilane); δ=7.92-7.65 (m, 15H, Ph$_3$S$^+$), 6.19 (s, 1H), 5.57 (s, 1H), 4.81 (t, J=16.0 Hz, 2H; CH$_2$), 1.92 (s, 3H)

$^{19}$F NMR (Solvent for measurement: Deuterated dimethyl sulfoxide, Reference material: Trichlorofluoromethane); δ=−114.49 (t, J=16.0 Hz, 2F; CF$_2$)

Example 2-1

Synthesis of triethylammonium 1,1,2,2-tetrafluoro-4-hydroxy-butane-1-sulfinate

1$^{st}$ Step: Sulfination Step

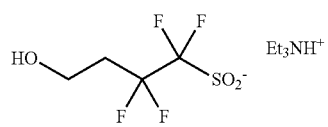

A 1 L reactor was charged with 100.0 g (0.44 mole/1.0 equivalent) of 4-bromo-3,3,4,4-tetrafluorobutan-1-ol, 300 g of acetonitrile, 250 g of water, 108.2 g (0.62 mole/1.4 equivalent) of sodium dithionite and 53.4 g (0.52 mole/1.2 equivalents) of triethylamine, followed by 4 hours of stirring at 60° C. Upon confirming the termination of the reaction, the reaction liquid underwent cooling and 100 mL of 1N HCl was added thereto, followed by stirring. Subsequently, an organic layer was separated, and then the organic layer was subjected to distillation of the solvent, thereby obtaining 264 g of a target triethylammonium 1,1,2,2-tetrafluoro-4-hydroxy-butane-1-sulfinate. It exhibited a purity of 46% and a yield of 88% at this time.

An obtained crude product was added in an amount of 150.0 g (46% purity, 69.0 g content, 0.222 millimoles/1.0 equivalent) to 750 mL of acetone, followed by 1 hour of stirring at room temperature. Thereafter, filteration was performed in the use of a filter paper. An obtained filtrate was concentrated and dried, thereby obtaining 66.0 g of a target triethylammonium 1,1,2,2-tetrafluoro-4-hydroxy-butane-1-sulfinate. It exhibited a purity of 93%, a content of 61.4 g or 0.197 mole and a yield of 89% at this time.

Properties of triethylammonium 1,1,2,2-tetrafluoro-4-hydroxy-butane-1-sulfinate $^1$H NMR (Solvent for measurement: Deuterated dimethyl sulfoxide, Reference material: Tetramethylsilane); δ=3.58 (t, 2H), 3.04 (q, 6H), 2.30 (m, 2H), 1.16 (t, 9H)

$^{19}$F NMR (Solvent for measurement: Deuterated dimethyl sulfoxide, Reference material: Trichlorofluoromethane); δ=−110.4 (t, 2F), −131.0 (s, 2F)

Example 2-2

Synthesis of triethylammonium 1,1,2,2-tetrafluoro-4-hydroxy-butane-1-sulfonate

2$^{nd}$ Step: Oxidation Step

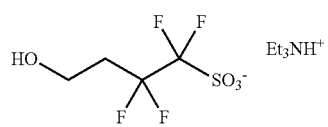

A 500 mL reactor was charged with 65 g (93% purity, 0.194 mole/1.0 equivalent) of triethylammonium 1,1,2,2-tetrafluoro-4-hydroxy-butane-1-sulfinate obtained in Example 2-1 by purification, 200 g of water and 46 g (0.40 mole/2.1 equivalents) of 30% hydrogen peroxide at room temperature, followed by 6 hours of stirring at 40° C. Upon confirming the termination of the reaction, the reaction liquid underwent cooling, and 7.5 g of sodium sulfite was added to the reaction liquid, followed by stirring. Thereafter, 350 g of acetone was added to a liquid obtained by distilling the solvent out of the reaction liquid, followed by 1 hour of stirring at room temperature. Thereafter, filteration was performed in the use of a filter paper. An obtained filtrate was concentrated and dried, thereby obtaining 65.6 g of a target triethylammonium 1,1,2,2-tetrafluoro-4-hydroxy-butane-1-sulfonate. It exhibited a purity of 92% and a yield of 95% at this time.

Properties of triethylammonium 1,1,2,2-tetrafluoro-4-hydroxy-butane-1-sulfonate $^1$H NMR (Solvent for measurement: Deuterated dimethyl sulfoxide, Reference material: Tetramethylsilane); δ=3.61 (t, 3H), 3.07 (q, 6H), 2.40 (m, 2H), 1.17 (t, 9H)

$^{19}$F NMR (Solvent for measurement: Deuterated dimethyl sulfoxide, Reference material: Trichlorofluoromethane); δ=−110.9 (s, 2F), −117.9 (s, 2F)

Example 2-3

Synthesis of triethylammonium 1,1,2,2-tetrafluoro-4-(2-methyl-acryloyloxy)-butane-1-sulfonate 3$^{rd}$ Step: Esterification Step

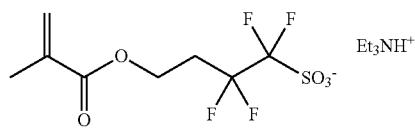

A 500 mL reactor was charged with 20.0 g (92% purity, 0.056 mole/1.0 equivalent) of triethylammonium 1,1,2,2-tetrafluoro-4-hydroxy-butane-1-sulfonate, 130.0 g of acetonitrile, 28.4 g (0.185 mole/3.3 equivalent) of methacrylic anhydride, 28.0 g (0.28 mole/5.0 equivalents) of triethylamine and 0.1 g of nonflex MBP (2,2'-methylene-bis(4-methyl-6-tert-butylphenol)), followed by 7 hours of stirring at 50° C. Then, the reaction liquid underwent cooling, and 200 g of water was added thereto, followed by 30 minutes of stirring. Thereafter, a volatile component was distilled out of the reaction liquid by heating under a reduced pressure. An obtained liquid was rinsed with 200 g of diisopropyl ether three times, thereby obtaining a target triethylammonium 1,1,2,2-tetrafluoro-4-(2-methyl-acryloyloxy)-butane-1-sulfonate in the form of an aqueous solution. An obtained target compound was brought into the next step without purification.

Example 2-4

Synthesis of triphenylsulfonium 1,1,2,2-tetrafluoro-4-(2-methyl-acryloyloxy)-butane-1-sulfonate 4$^{th}$ Step: Onium Salt-Exchanging Step

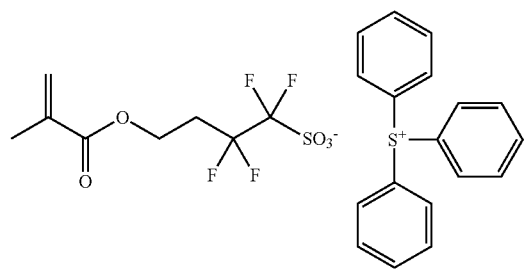

A 100 mL reactor was charged with the aqueous solution of triethylammonium 1,1,2,2-tetrafluoro-4-(2-methyl-acryloyloxy)-butane-1-sulfonate obtained by the 3$^{rd}$ step, and a solution of 20.2 g (0.056 mole) of triphenylsulfonium bromide and 100 g of chloroform, followed by 3 hours of stirring at room temperature. Subsequently, an organic layer was separated, and the thus obtained organic layer was rinsed with 100 g of water four times. Subsequently, it was rinsed with 100 g of diisopropyl ether three times thereby precipitating a solid. Upon performing filteration, the solid was dried, thereby obtaining 32.5 g of a target triphenylsulfonium 1,1,2,2-tetrafluoro-4-(2-methyl-acryloyloxy)-butane-1-sulfonate. It exhibited a purity of 93% at this time (most of a balance of 7% was the solvent, i.e., diisopropyl ether), and a yield of 97% taken over from the 3$^{rd}$ step.

Comparative Example 1

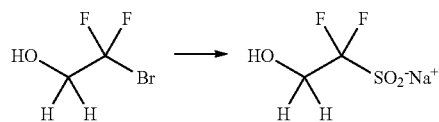

A solution containing 8.92 g (55.4 millimoles) of 2-bromo-2,2-difluoroethanol, 12 g of acetonitrile and 22 g of water was prepared, and 5.43 g (64.6 millimoles) of sodium hydrogencarbonate and 9.69 g (55.6 millimoles) of sodium dithionite was added thereto. This liquid, which was separated into two layers, was stirred at 60° C. for 12 hours. Upon cooling the liquid down to room temperature, a solvent (an organic layer and water layer) was distilled off, followed by drying, thereby obtaining 7.0 g of a white solid. The solid was analyzed by nuclear magnetic resonance (NMR), with which it was found that the content of a target sodium 1,1-difluoro-2-hydroxy-ethanesulfinate was about 8% and the yield obtained by converting the content was 6%.

Comparative Example 2

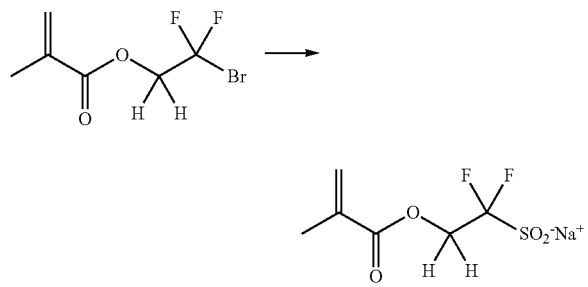

A glass flask equipped with a thermometer and a condenser was charged with 5 g (21.8 millimoles) of 2-bromo-2,2-difluoroethyl(2-methylacrylate), 40 g of acetonitrile and 40 g of water, followed by stirring. Then, 2.2 g (26.2 millimoles) of sodium hydrogencarbonate and 5.7 g (32.7 millimoles) of sodium dithionite were added thereto, followed by 2 hours of stirring at 60° C. An organic layer of a reaction liquid was analyzed by using nuclear magnetic resonance (NMR), with which it was found that a target sodium 1,1-difluoro-2-(2-methacryloyloxy)-ethanesulfinate was not detected but a by-product formed due to a decomposed methacrylic moiety was the only one detected.

Comparative Example 3

Synthesis of triethylammonium 1,1,2,2-tetrafluoro-4-hydroxy-butane-1-sulfonate $2^{nd}$ Step: Oxidation Step A 500 mL reactor was charged with 112 g (46% purity, 0.17 moles) of triethylammonium 1,1,2,2-tetrafluoro-4-hydroxy-butane-1-sulfinate, 200 g of water and 41 g (0.36 mole) of 30% hydrogen peroxide, at room temperature, followed by 6 hours of stirring at 40° C. Upon confirming the termination of the reaction, a reaction liquid underwent cooling and 7.5 g of sodium sulfite was added to the reaction liquid, followed by stirring. Subsequently, a liquid obtained by distilling the solvent out of the reaction liquid was rinsed with 50 g of hexane, and then extracted with 100 g of chloroform. It was heated under a reduced pressure so as to distill a volatile component off and then dried, thereby obtaining 43 g of a target triethylammonium 1,1,2,2-tetrafluoro-4-hydroxy-butane-1-sulfonate. It exhibited a purity of 50% and a yield of 40% at this time. As a result of analysis, it was found that 4-bromo-3,3,4,4-tetrafluorobutan-1-ol which had been confirmed to disappear by the $1^{st}$ step (sulfination step) was formed during this $2^{nd}$ step (oxidation step) as a by-product in an amount of 9%.

The invention claimed is:

1. A method for synthesizing an onium fluoroalkanesulfonate represented by general formula [5]

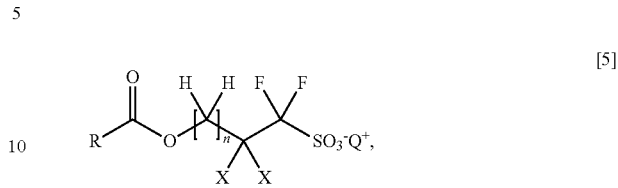

comprising the steps of:

(1) a sulfination step of reacting a bromofluoroalcohol represented by general formula [1]

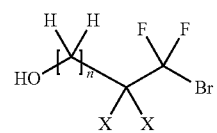

with a sulfinating agent in the presence of amine, thereby obtaining an ammonium hydroxyfluoroalkanesulfinate represented by general formula [2]

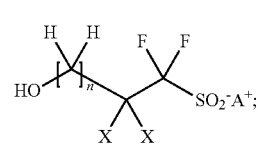

(2) an oxidation step of reacting the ammonium hydroxyfluoroalkanesulfinate represented by general formula [2] and obtained by the $1^{st}$ step (the sulfination step) with an oxidizing agent thereby obtaining the ammonium hydroxyfluoroalkanesulfonate represented by general formula [3]

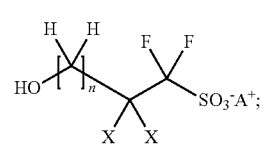

(3) an esterification step of reacting the ammonium hydroxyfluoroalkanesulfonate represented by general formula [3] and obtained by step (2) with a carboxylic acid derivative represented by general formula [6]

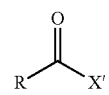

or general formula [7]

$$R\underset{O}{\overset{O}{\|}}C-O-\underset{O}{\overset{O}{\|}}C R, \quad [7]$$

thereby obtaining an ammonium fluoroalkanesulfonate represented by general formula [4]

$$R-\underset{O}{\overset{O}{\|}}C-O-\left[\underset{H}{\overset{H}{C}}\right]_n-\underset{X}{\overset{F}{C}}\underset{X}{\overset{F}{-C}}-SO_3^-A^+; \text{ and} \quad [4]$$

(4) performing an onium salt-exchange by using a monovalent onium salt represented by general formula [8]

$$Q^+ X^-, \quad [8]$$

wherein $A^+$ represents an ion selected from the group consisting of methylammonium ion ($MeNH_3^+$), dimethylammonium ion ($Me_2NH_2^+$), trimethylammonium ion ($Me_3NH^+$), ethylammonium ion ($EtNH_3^+$), diethylammonium ion ($Et_2NH_2^+$), triethylammonium ion ($Et_3NH^+$), n-propylammonium ion (n-$PrNH_3^+$), di-n-propylammonium ion (n-$Pr_2NH_2^+$), tri-n-propylammonium ion (n-$Pr_3NH^+$), i-propylammonium ion (i-$PrNH_3^+$), di-i-propylammonium ion (i-$Pr_2NH_2^+$), tri-i-propylammonium ion ($Me_3NH^+$), n-butylammonium ion (n-$BuNH_3^+$), di-n-butylammonium ion (n-$Bu_2NH_2^+$), tri-n-butylammonium ion (n-$Bu_3NH^+$), sec-butylammonium ion (sec-$BuNH_3^+$), di-sec-butylammonium ion (sec-$Bu_2NH_2^+$), tri-sec-butylammonium ion (sec-$Bu_3NH^+$), tert-butylammonium ion (t-$BuNH_3^+$), di-tert-butylammonium ion (t-$Bu_2NH_2^+$), tri-tert-butylammonium ion (t-$Bu_3NH^+$), diisopropylethylammonium (i-$Pr_2EtNH^+$), phenylammonium ion ($PhNH_3^+$), diphenylammonium ion ($Ph_2NH_2^+$), triphenylammonium ion ($Ph_3NH^+$), ions having the following structures:

and mixtures thereof;

X mutually independently represents a hydrogen atom or fluorine atom;

n represents an integer of 0 to 8;

X' represents a hydroxyl group or a halogen;

R represents a linear or branched alkyl group having 1 to 10 carbon atoms, a linear or branched alkenyl group having 1 to 10 carbon atoms and a polymerizable double bond at least at the end moiety, an alicyclic organic group having 3 to 20 carbon atoms, an organic group having 3 to 20 carbon atoms and containing an alicyclic organic group and a linear alkylene group, a monocyclic or polycyclic lactone having 3 to 30 carbon atoms, or an aryl group having 6 to 20 carbon atoms, wherein one or more hydrogen atoms in the alkyl group, the alkenyl group, the alicyclic organic group, the organic group containing the alicyclic organic group and the linear alkylene group, the monocyclic or polycyclic lactone or the aryl group may be substituted with fluorine, a hydroxyl group, a hydroxycarbonyl group, or a linear, branched or cyclic alkoxy group having 1 to 6 carbon atoms, two hydrogen atoms on the same carbon that constructs the alkyl group, the alkenyl group, the alicyclic organic group, or the organic group containing the alicyclic organic group and the linear alkylene group may be substituted with one oxygen atom to form a keto group, and one hydrogen atom on the alkyl group may be substituted with 2-acryloyloxy group, a 2-methacryloyloxy group or a 2-trifluoromethacryloyloxy group;

$Q^+$ represents a sulfonium cation of general formula (a) or general formula (b), or an iodonium cation of general formula (c)

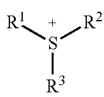 (a)

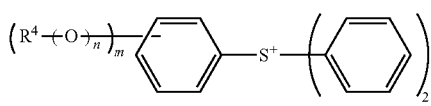 (b)

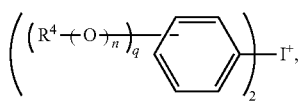 (c)

wherein
- R¹, R² and R³ mutually independently represent a substituted or unsubstituted linear or branched alkyl group, alkenyl group or oxoalkyl group having 1 to 10 carbon atoms, or a substituted or unsubstituted aryl group, aralkyl group or aryloxoalkyl group having 6 to 18 carbon atoms; or two or more of R¹, R² and R³ may bond to each other to form a ring together with a sulfur atom;
- R⁴ represents a substituted or unsubstituted linear, branched or cyclic alkyl group or alkenyl group having 1 to 20 carbon atoms, or a substituted or unsubstituted aryl group having 6 to 14 carbon atoms;

m represents an integer of 1 to 5;
q represents an integer of 0 (zero) to 5, and
n represents 0 (zero) or 1 in general formula (b) and general formula (c).

2. A method as claimed in claim 1, wherein, in general formula [1] to general formula [5], n is 2 and both of the two X atoms are fluorine atoms.

3. A method as claimed in claim 1, wherein, in general formula [1] to general formula [5], n is 4 and both of the two X atoms are fluorine atoms.

4. A method as claimed in claim 1, wherein, in general formula [1] to general formula [5], n is 0 and both of the two X atoms are hydrogen atoms.

5. A method as claimed in claim 1, wherein the amine used in the sulfination step is an amine represented by general formula [I],

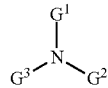 [1]

wherein G¹, G² and G³ mutually independently represent a hydrogen atom, an alkyl group having 1 to 6 carbon atoms, an alkoxyalkyl group having 1 to 6 carbon atoms, a cycloalkyl group having 3 to 12 carbon atoms, a substitution-acceptable phenyl group, a substitution-acceptable aralkyl group having 7 to 12 carbon atoms, a substitution-acceptable naphthyl group, or a substitution-acceptable heteroaromatic group having 5 to 10 carbon atoms, or wherein at least two or more of G¹, G² and G³ may form a ring which may include a heteroatom.

6. A method as claimed in claim 1, wherein R in general formula [4] to general formula [7] represents any one of polymerizable double bond-containing groups represented by the following formulas,

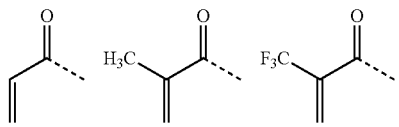

wherein each dotted line represents a bonding location.

7. An ammonium hydroxyfluoroalkanesulfinate represented by general formula [2],

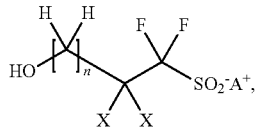 [2]

wherein A⁺ represents an ion selected from the group consisting of methylammonium ion (MeNH₃⁺), dimethylammonium ion (Me₂NH₂⁺), trimethylammonium ion (Me₃NH⁺), ethylammonium ion (EtNH₃⁺), diethylammonium ion (Et₂NH₂⁺), triethylammonium ion (Et₃NH⁺), n-propylammonium ion (n-PrNH₃⁺), di-n-propylammonium ion (n-Pr₂NH₂⁺), tri-n-propylammonium ion (n-Pr₃NH⁺), i-propylammonium ion (i-PrNH₃⁺), di-i-propylammonium ion (i-Pr₂NH₂⁺), tri-i-propylammonium ion (Me₃NH⁺), n-butylammonium ion (n-BuNH₃⁺), di-n-butylammonium ion (n-Bu₂NH₂⁺), tri-n-butylammonium ion (n-Bu₃NH⁺), sec-butylammonium ion (sec-BuNH₃⁺), di-sec-butylammonium ion (sec-Bu₂NH₂⁺), tri-sec-butylammonium ion (sec-Bu₃NH⁺), tert-butylammonium ion (t-BuNH₃⁺), di-tert-butylammonium ion (t-Bu₂NH₂⁺), tri-tert-butylammonium ion (t-Bu₃NH⁺), diisopropylethylammonium (i-Pr₂EtNH⁺), phenylammonium ion (PhNH₃⁺), diphenylammonium ion (Ph₂NH₂⁺), triphenylammonium ion (Ph₃NH⁺), ions having the following structures:

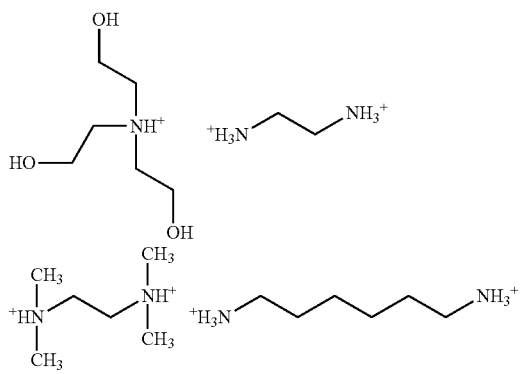

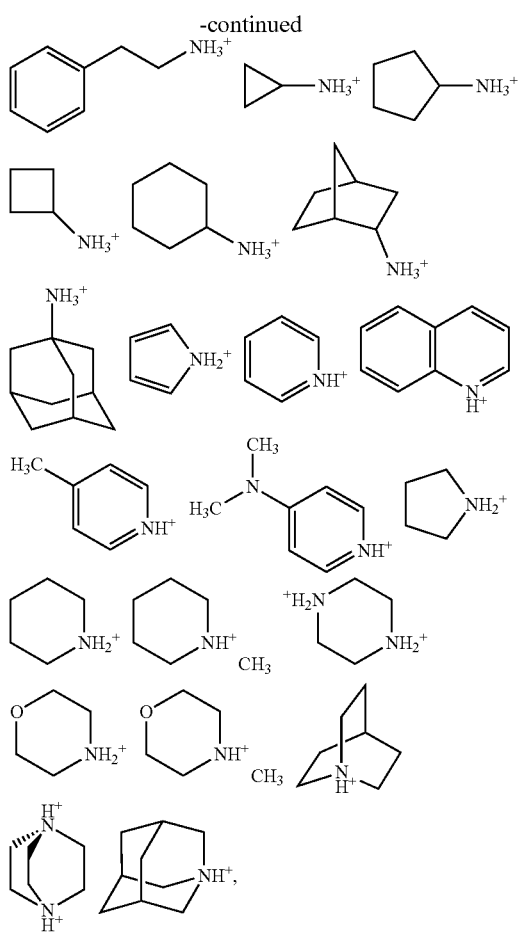

and mixtures thereof;
X mutually independently represents a hydrogen atom or fluorine atom; and
n represents an integer of 0 to 8.

8. An ammonium hydroxyfluoroalkanesulfonate represented by general formula [3]

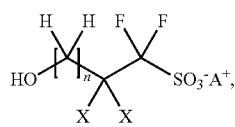

[3]

wherein $A^+$ represents an ion selected from the group consisting of methylammonium ion ($MeNH_3^+$), dimethylammonium ion ($Me_2NH_2^+$), trimethylammonium ion ($Me_3NH^+$), ethylammonium ion ($EtNH_3^+$), diethylammonium ion ($Et_2NH_2^+$), triethylammonium ion ($Et_3NH^+$), n-propylammonium ion ($n-PrNH_3^+$), di-n-propylammonium ion ($n-Pr_2NH_2^+$), tri-n-propylammonium ion ($n-Pr_3NH^+$), i-propylammonium ion ($i-PrNH_3^+$), di-i-propylammonium ion ($i-Pr_2NH_2^+$), tri-i-propylammonium ion ($Me_3NH^+$), n-butylammonium ion ($n-BuNH_3^+$), di-n-butylammonium ion ($n-Bu_2NH_2^+$), tri-n-butylammonium ion ($n-Bu_3NH^+$), sec-butylammonium ion ($sec-BuNH_3^+$), di-sec-butylammonium ion ($sec-Bu_2NH_2^+$), tri-sec-butylammonium ion ($sec-Bu_3NH^+$), tert-butylammonium ion ($t-BuNH_3^+$), di-tert-butylammonium ion ($t-Bu_2NH_2^+$), tri-tert-butylammonium ion ($t-Bu_3NH^+$), diisopropylethylammonium ($i-Pr_2EtNH^+$), phenylammonium ion ($PhNH_3^+$), diphenylammonium ion ($Ph_2NH_2^+$), triphenylammonium ion ($Ph_3NH^+$), ions having the following structures:

and mixtures thereof;
X mutually independently represents a hydrogen atom or fluorine atom; and
n represents an integer of 0 to 8.

9. A method as in claim 5, wherein the amine represented by general formula [1] is selected from the group consisting of trimethylamine, triethylamine, tri-n-propylamine, tri-i-propylamine, tri-n-butylamine, tri-sec-butylamine, tri-tert-butylamine, diisopropylethylamine, triphenylamine, and organic bases having the following structures:

10. A method for synthesizing an onium fluoroalkanesulfonate represented by general formula [5]

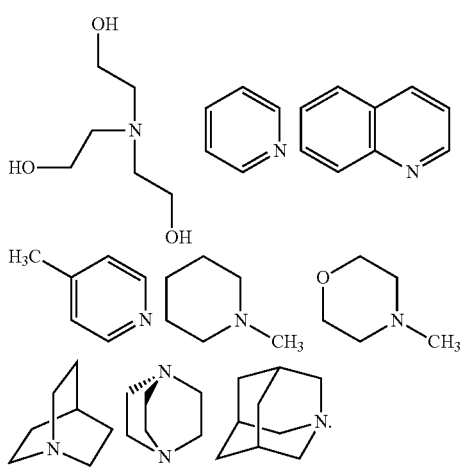

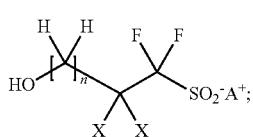

comprising the steps of:
(1) a sulfination step of reacting a bromofluoroalcohol represented by general formula [1]

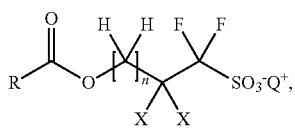

with a sulfinating agent in the presence of amine thereby obtaining an ammonium hydroxyfluoroalkanesulfinate represented by general formula [2]

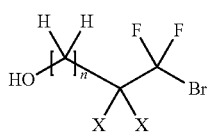

(2) an oxidation step of reacting the ammonium hydroxyfluoroalkanesulfinate represented by general formula [2] and obtained by step (1) with an oxidizing agent thereby obtaining the ammonium hydroxyfluoroalkanesulfonate represented by general formula [3]

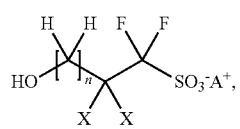

(3) an esterification step of reacting the ammonium hydroxyfluoroalkanesulfonate represented by general formula [3] and obtained by step (2) with a carboxylic acid derivative represented by general formula [6]

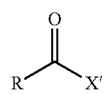

or general formula [7]

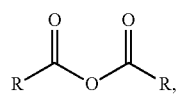

thereby obtaining an ammonium fluoroalkanesulfonate represented by general formula [4]

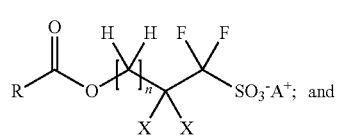

(4) performing an onium salt-exchange by using a monovalent onium salt represented by general formula [8]
$Q^+X^-$, wherein the amine used in the sulfination step is triethylamine;
wherein $A^+$ represents triethylammonium ion ($Et_3NH^+$);
X mutually independently represents a hydrogen atom or fluorine atom;
n represents an integer of 0 to 2; in general formula [6],
X' represents a hydroxyl group or a halogen;
R represents vinyl group or 1-methylethenyl group; and
$Q^+$ represents triphenylsulfonium.

* * * * *